US007630752B2

(12) United States Patent
Viswanathan

(10) Patent No.: US 7,630,752 B2
(45) Date of Patent: Dec. 8, 2009

(54) REMOTE CONTROL OF MEDICAL DEVICES USING A VIRTUAL DEVICE INTERFACE

(75) Inventor: Raju R. Viswanathan, Clayton, MO (US)

(73) Assignee: Stereotaxis, Inc., St. Louis, MO (US)

(*) Notice: Subject to any disclaimer, the term of this patent is extended or adjusted under 35 U.S.C. 154(b) by 1345 days.

(21) Appl. No.: 10/448,273

(22) Filed: May 29, 2003

(65) Prior Publication Data

US 2004/0068173 A1    Apr. 8, 2004

Related U.S. Application Data

(60) Provisional application No. 60/401,670, filed on Aug. 6, 2002.

(51) Int. Cl.
*A61M 25/00* (2006.01)
*A61F 11/00* (2006.01)
*A61B 5/05* (2006.01)

(52) U.S. Cl. .................. 600/409; 600/424; 606/108

(58) Field of Classification Search .......... 600/431, 600/242; 606/108
See application file for complete search history.

(56) References Cited

U.S. PATENT DOCUMENTS

| | | | | |
|---|---|---|---|---|
| 6,015,414 A | * | 1/2000 | Werp et al. | 606/108 |
| 6,138,495 A | * | 10/2000 | Paltieli et al. | 73/1.86 |
| 6,167,296 A | * | 12/2000 | Shahidi | 600/427 |
| 6,213,974 B1 | * | 4/2001 | Smith et al. | 604/95.01 |
| 6,272,370 B1 | * | 8/2001 | Gillies et al. | 600/411 |
| 6,285,902 B1 | * | 9/2001 | Kienzle et al. | 600/427 |
| 6,470,207 B1 | * | 10/2002 | Simon et al. | 600/426 |
| 6,755,816 B2 | * | 6/2004 | Ritter et al. | 606/1 |
| 2001/0031919 A1 | * | 10/2001 | Strommer et al. | 600/424 |
| 2001/0039426 A1 | * | 11/2001 | Makower et al. | 606/153 |
| 2002/0052546 A1 | * | 5/2002 | Frantz et al. | 600/424 |
| 2002/0183723 A1 | * | 12/2002 | Belef et al. | 606/1 |
| 2003/0018251 A1 | * | 1/2003 | Solomon | 600/427 |
| 2003/0028091 A1 | * | 2/2003 | Simon et al. | 600/407 |
| 2003/0074011 A1 | * | 4/2003 | Gilboa et al. | 606/130 |

* cited by examiner

*Primary Examiner*—Eric F Winakur
*Assistant Examiner*—Helene Bor
(74) *Attorney, Agent, or Firm*—Harness, Dickey & Pierce, P.L.C.

(57) ABSTRACT

An interface system and method for controlling a magnetic surgery system by displaying a virtual image of the device, adjusting the configuration of the device or the actuation controls to be applied to the device until the configuration of the displayed device assumes the configuration desired by the user, or selecting a desired target location for the tip, and causing a set of actuation controls to be applied to the actual device to cause the actual device to assume the configuration of the virtual device or to steer the device tip to the desired location.

60 Claims, 18 Drawing Sheets

92    100         94              96

REMOTE CONTROL OF MEDICAL DEVICES USING A VIRTUAL DEVICE INTERFACE

CROSS-REFERENCE TO RELATED APPLICATION

This application claims priority of prior provisional application Ser. No. 60/401,670, filed Aug. 6, 2002, entitled Method and Apparatus for Improved Magnetic Surgery Employing Virtual Device Interface, the disclosure of which is incorporated by reference in its entirety.

BACKGROUND OF THE INVENTION

This invention relates to the remote control of medical devices in a subject's body, and in particular to a user interface for operating a remotely controllable medical device which employs a "virtual device" interface.

Advances in technology have resulted in systems that allow a physician or other medical professional to remotely control the orientation of the distal end of a medical device. It is now fairly routine to steer the distal end of a medical device inside a subject's body by mechanically manipulating controls on the proximal end of the medical device. Recently magnetic navigation systems have been developed that allow a physician to orient the distal end of a medical device using the field of an external source magnet. Other systems have been developed for the automated remote orientation of the distal end of a medical device, for example by operating magnetostrictive or electrostrictive elements incorporated into the medical device. However the medical device is controlled, it can still be difficult for a physician to visualize the procedure site (which is out of view inside the patient's body), to selected the desired direction in which to orient the distal end of the medical device and communicate the selected direction to the system in order to orient the distal end of the medical device in the selected direction.

As stated above, magnetic navigation systems have been developed which apply a controlled magnetic field to an operating region in a subject, to orient a magnetically responsive element on a medical device in the operating region. Examples of such systems include Ritter et al., U.S. Pat. No. 6,241,671, issued Jun. 5, 2001, for Open Field System For Magnetic Surgery (incorporated herein by reference). Magnetic navigation systems permit faster and easier navigation, and allow the devices to be made thinner and more flexible than conventional mechanically navigated devices which must contain pull wires and other components for steering the device. Because of the advances made in magnetic surgery systems and magnetically responsive medical devices, the determination of the appropriate field direction, and instructing the magnetic surgery system to apply the determined magnetic field are probably the most difficult tasks remaining in magnetically assisted medical procedures. Significant efforts have been made to help the user to visualize the procedure, and improve the user's ability to control the magnetic surgery system during the procedure. There is often a lag between the direction of the applied field, and the actual direction of the distal end of the medical device. In some current systems, the user specifies a field direction, and mentally must take into account the lag between the applied field and the actual device direction.

SUMMARY OF THE INVENTION

This invention provides a method and apparatus for controlling a flexible medical device in a subject's body which employs a virtual device interface, i.e. an interface using a physical or computational model of the actual device, possibly including a computerized control interface for real-time/interactive navigational control of the device. Such a computerized device control interface would accept user input from an input device (for example, a joystick) and interpret these inputs through a computer to apply appropriate controls to drive the device tip according to a pre-defined mapping. Generally the method of this invention comprises displaying an image of the distal end portion of a "virtual" medical device, and allowing the user to manipulate the displayed image of the distal end portion of the virtual medical device into a desired configuration (shape and/or orientation), and then remotely operate the device to cause the distal end portion of the actual medical device to assume the desired configuration represented by the image of the virtual device.

In a preferred embodiment of the system and method of this invention, the configuration of the displayed virtual medical device can be controlled by identifying a target point to which the virtual medical device configures itself to. In another preferred embodiment, controls that change the shape of virtual medical device, e.g., a deflection control and a rotation control are used to control configuration. In still another preferred embodiment of the system and method of this invention, the configuration of the displayed virtual medical device can be changed by changing at least one control parameter (e.g., the applied magnetic field for a magnetically controlled device) and updating the image of the virtual medical device to show the configuration of the distal end of the virtual medical device "as if" the at least one control parameter was changed (in the particular case of a magnetically controlled device, as if the new field were applied). In another preferred embodiment, the user can identify a target location and the interface uses the virtual device model to determine the control parameter(s) to cause the actual device to reach the target. In still another alternate preferred embodiment of the system and method of this invention, a surface of points of the possible positions of the distal end of the medical device is displayed. The user can then select a point on the surface, and operate the system to automatically apply the correct magnetic field to cause the distal end of the medical device to align in the direction of the selected point.

A preferred embodiment of this invention provides an interface system and method for facilitating the specification and application of a magnetic field to the operating region in a subject to control the distal end of a medical device in the operating region. This invention can provide a method and apparatus for controlling a magnetic navigation system, and in particular provides an interface system and method for facilitating the specification and application of a magnetic field to the operating region in a patient to control the distal end of a magnetically enabled medical device in the operating region. However, the virtual device interface of the present invention is not so limited, and can be used with any system for controlling the configuration of a medical device and actuated by any of a variety of means. Furthermore, the interface can be used with any elongate medical device, including guide wires, catheters, and endoscopes, etc.

The system and method of this invention allows the user to visualize the configuration of the distal end portion of the medical device before actually applying the control variable(s) used to modify the configuration of the device. This is faster and easier to learn and to operate than many current user interfaces; for instance some present magnetic navigation interfaces require the user to specify a magnetic field direction without reference to the current orientation of the distal end portion of the medical device. This also facilitates automating the procedure combining directional control with an advancer for advancing the medical device. Furthermore the present invention lets the user directly manipulate the distal end of the device in an interactive manner through the use of an input device whose manipulation by the user is mapped by a computer to changes in actuation control variables which then produce a corresponding change in device configuration. The change in device configuration may be visually displayed to the user through the use of any of a variety of imaging systems so that the user has interactive control over the device. The input device for this purpose may for example be a joystick, graphical menu buttons, keyboard buttons, or any other choice that is known to those skilled in the art. The mapping of input device manipulations to changes in device actuation controls may be chosen in a variety of ways that provide intuitive spatial control of the device. A selection of possible mapping choices can be offered to the user so that the user can pick the one that she or he deems most appropriate in a given navigational circumstance. These and other features and advantages will be in part apparent, and in part pointed out hereinafter.

BRIEF DESCRIPTION OF THE DRAWINGS

Corresponding reference numerals indicate corresponding parts throughout the several views of the drawings.

DETAILED DESCRIPTION OF THE INVENTION

The virtual device interface of the present invention can be used with any type of remotely controllable medical device, including for example mechanically, electrically, and magnetically actuatable medical devices. One possible use of the invention is in the control of magnetically actuatable devices, such as with the magnetic navigation system shown in FIG. 1. While described below primarily in connection with a preferred embodiment in the form of a magnetic surgery system in conjunction with an X-ray imaging system, this invention is not so limited. For example, a Magnetic Resonance imaging system could be used, with the catheter being steered by torques generated by the use of changeable magnetic moments located on the device that interact with the static magnetic field of the Magnetic Resonance imaging system. Likewise, any other imaging modality or actuation modality could be employed.

Figure 1:
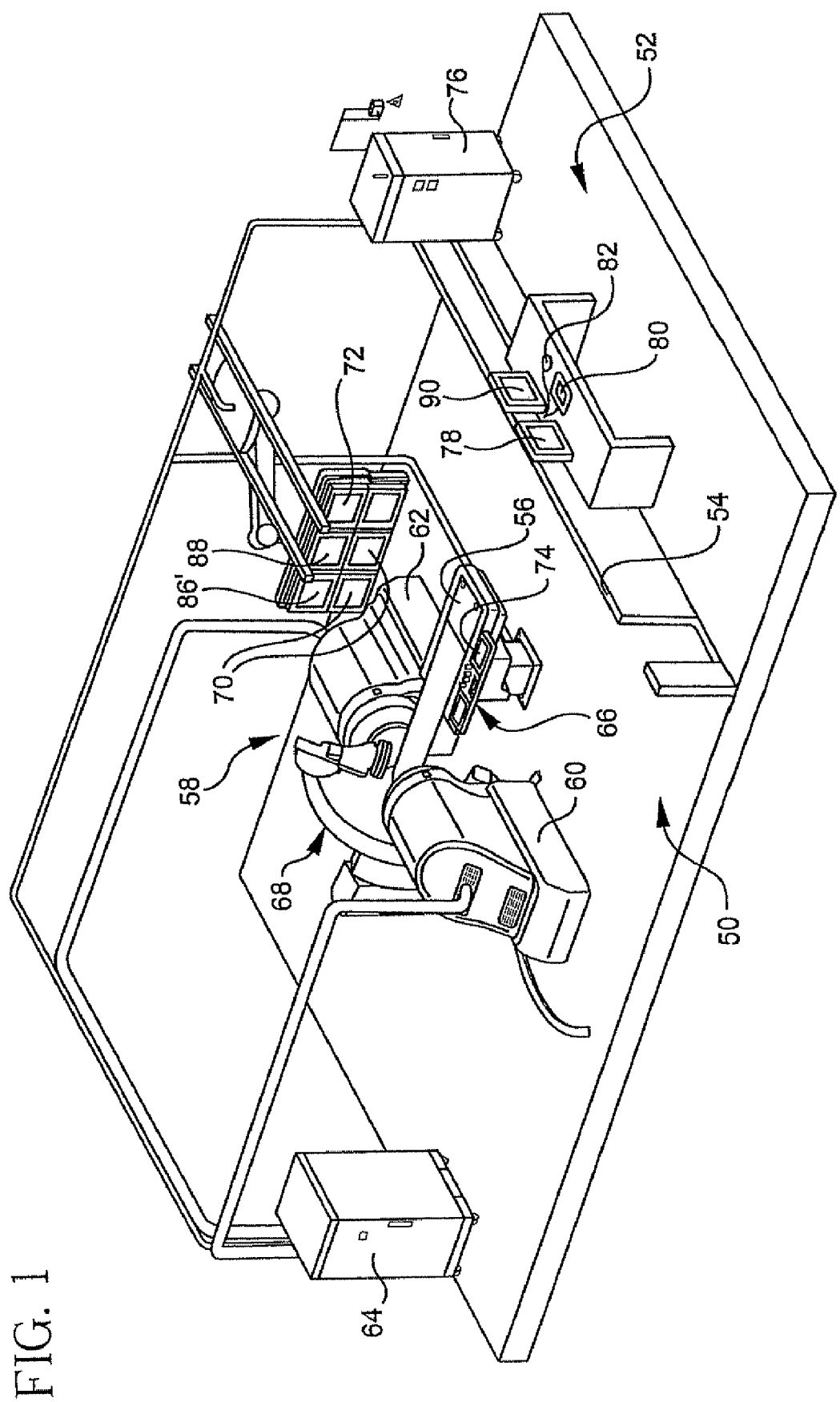
FIG. 1 is a schematic view of magnetic surgery system incorporating the interface system of the present invention.

As shown in FIG. 1, a magnetic surgery system is set up in the procedure room 50 where the patient is located, and in a control room 52. The control room 52 is preferably adjacent the procedure room 50, and there may be a window 54 between the control room and the procedure room to permit direct observation of the patient, however the control room could be remote from the patient, and with the aid of the present interface, a physician could conduct a procedure on a patient in the procedure from a control room on a different floor, in a different building, or even in a different city.

The magnetic surgery system comprises a patient bed 56, and a magnetic navigation system 58 comprising opposed magnet units 60 and 62 on opposite sides of the patient bed operated by a processor 64 and controlled by controls 66 adjacent the patient 56. An imaging system 68, such as an x-ray imaging system on a C-arm, displays images of the operating region on a set of monitors 70 in the procedure room 50. The interface system of the present invention provides a convenient way for a user to operate the magnetic navigation system 58 to control the distal end of a medical device in the operating region inside the patient's body.

The interface includes a display on, for example, an lcd monitor 72, and a digital tablet 74 in the procedure room 50, a processor 76, a display on, for example, monitor 78, a key board 80, and a mouse/digital tablet 82 in the control room 54. Additional displays on monitors 86 and 88 can be provided in the procedure room 50 which integrate images from the imaging system 68 with the interface. One or more additional monitors 90 can be provided in the control room so that the images are available in the control room as well. The monitor 90 preferably displays a multi-pane display.

Figure 2:
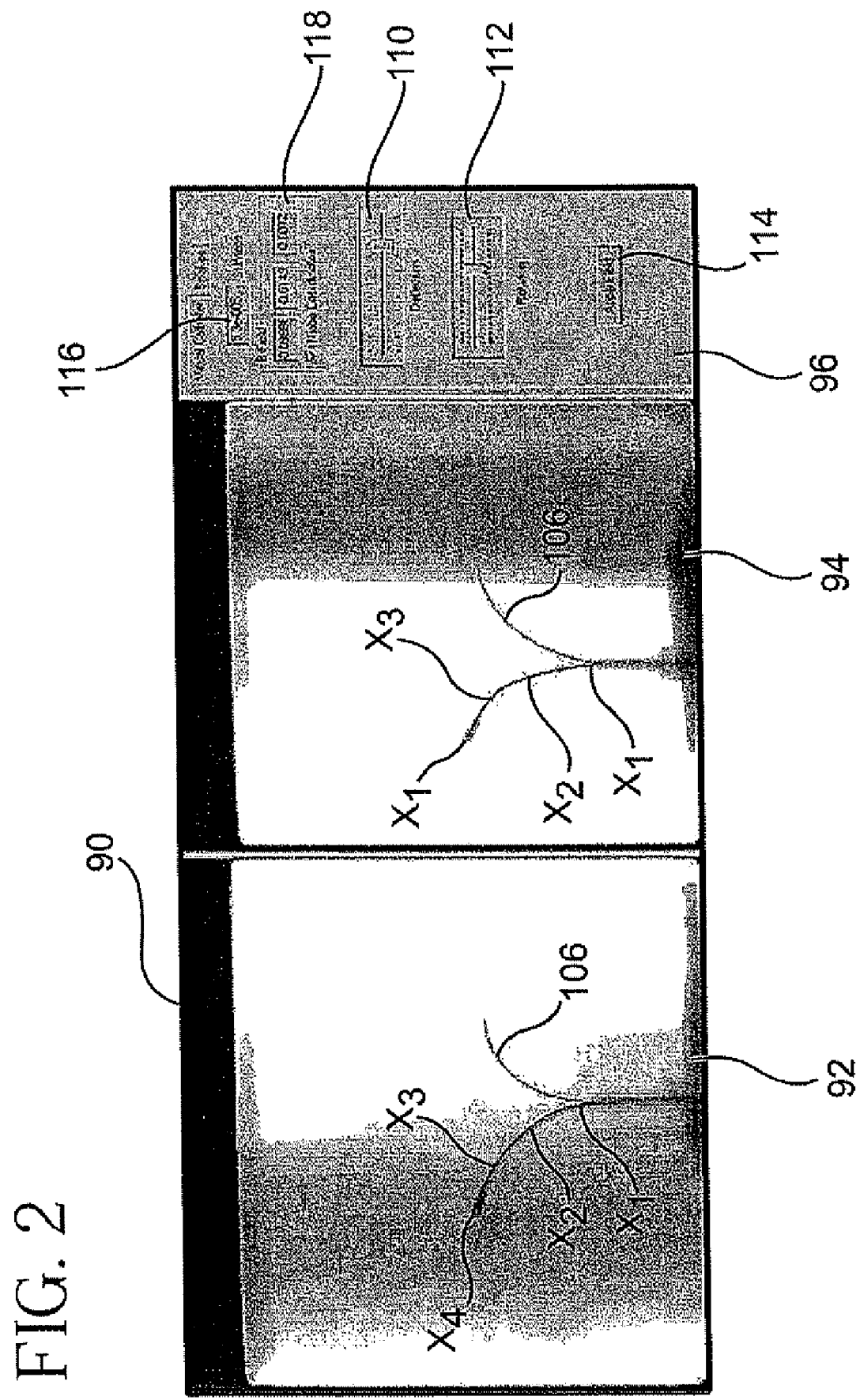
FIG. 2 is a schematic view of a possible display screen for implementing the interface system for a magnetic surgery system constructed according to the principles of a preferred embodiment of this invention.

In one preferred embodiment of this invention as shown in FIG. 2, one of the displays, for example display 90 has panes 92 and 94 for receiving biplane images of the operating region. The display 90 preferably also includes a control pane 96. As shown in FIG. 2, the user selects a discrete set of points on the distal end of the medical device to characterize the device. In the preferred embodiment, the operating region is imaged with a bi-planar imaging (such as bi-plane fluoroscopy), providing two images of the operating region and of the distal end of the medical device, in different, and preferably mutually perpendicular, planes. For example, the bi-plane imaging system might provide left anterior oblique (LAO) and right anterior oblique (RAO) images of the operating region, in panes 92 and 94, respectively. Bi-plane imaging could be provided with a single x-ray source and imaging plate that are moved in tandem to provide imaging in multiple planes.

The user preferably identifies the "support" point or "pivot" point $x_1$ of the distal end portion of the medical device on each of the panes 92 and 94. By identifying the point in both planes, the user has uniquely identified the point in three dimensional space. The user preferably also identifies the distal end $x_4$ of the medical device. The user preferably also identifies at least one, and preferably at least two other points $x_2$ and $x_3$, between points $x_1$ and $x_4$. The user could of course identify more points, but the additional accuracy achieved usually does not outweigh the inconvenience to the user.

Other methods of reconstructing the shape of the distal end of the medical device are possible. For example, points could be identified independently on each of the views. Based upon the these points the processor could develop splines (a sequence of polynomial curves) for each plane, and then identify corresponding points on the two splines to characterize the shape of the medical device in three dimensions.

Figure 4A:
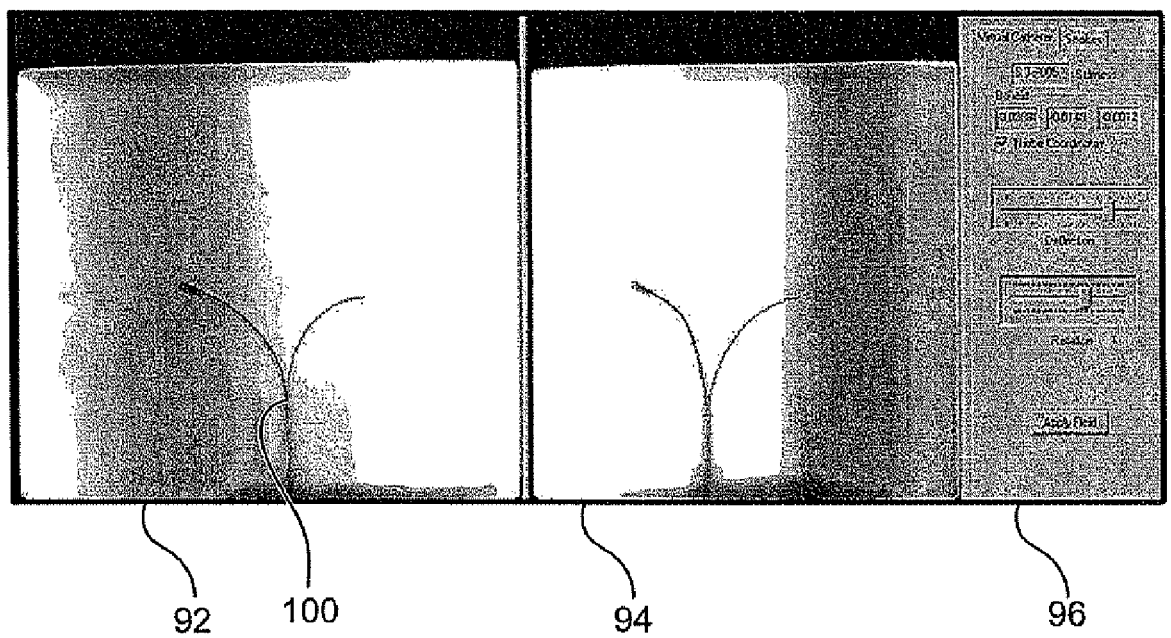
FIG. 4A is a schematic view of the bi-plane imaging displays from the interface shown in FIG. 2, illustrating the identification of a point.
Figure 4B:
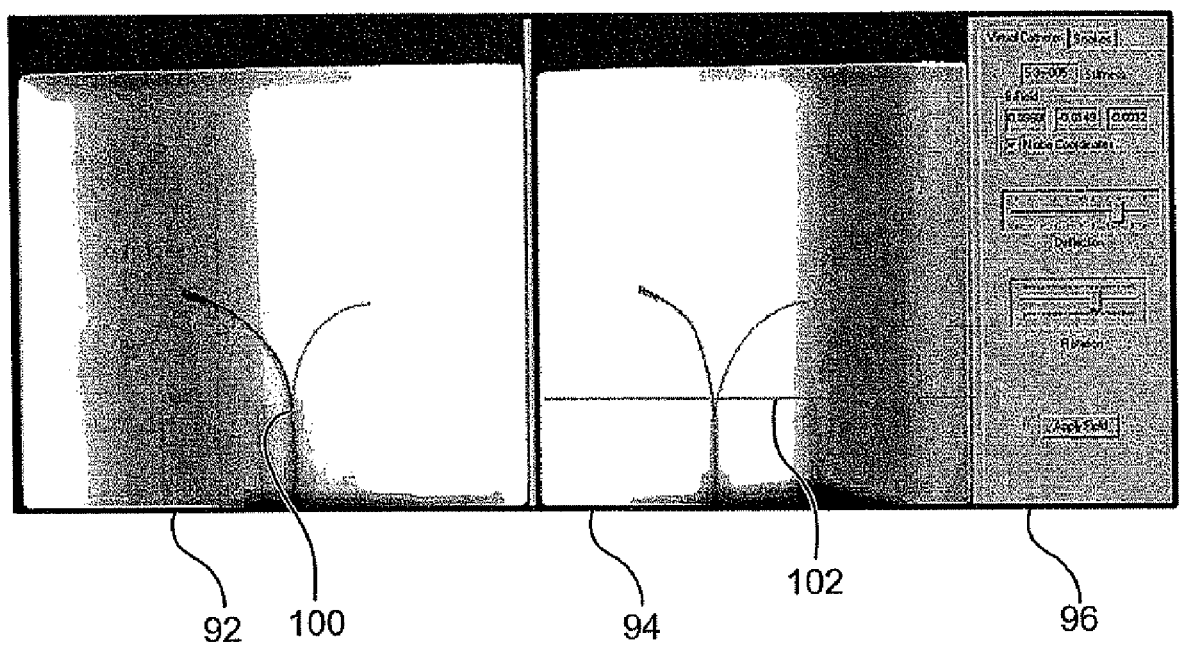
FIG. 4B is a schematic view of the bi-plane imaging displays from the interface shown in FIG. 2, illustrating the identification of a point.
Figure 4C:
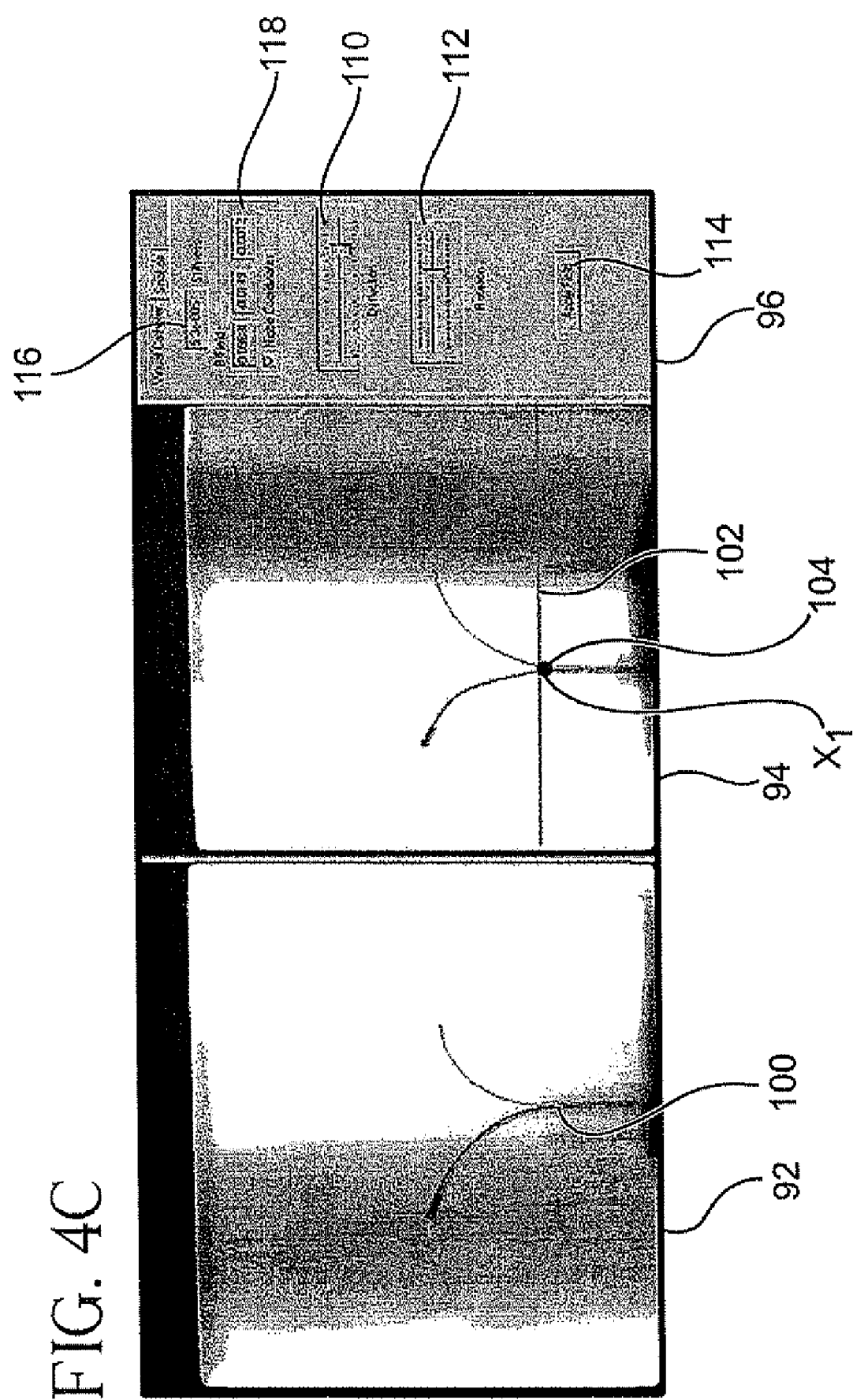
FIG. 4C is a schematic view of the bi-plane imaging displays from the interface shown in FIG. 2, illustrating the identification of a point.

As shown in FIG. 4A, the points can be identified by manipulating a cursor on each of the bi-planar displays, and clicking on a point, such as point 100. As shown in FIG. 4B, after the user clicks on point 100 on the LAO, a line 102 is displayed on the RAO, along which the point 100 identified in the LAO must lie. As shown in FIG. 4C, the user then uniquely identifies the point in three dimensional space by identifying the desired point 104 along the line 102 displayed on the RAO. The user could begin on the RAO, and complete the point identification process in the LAO. Some other method can be used to identify points, or the points can be identified automatically, for example using image processing.

Of course, instead of using bi-plane images to uniquely identify points on the medical device to characterize the shape of the medical device, a localization system could be employed to characterize the shape of the medical device. For example a magnetic localization system employing reference transmitters in the procedure room can transmit to one or more receivers on the medical device to locate the receiver and thus the medical device in three-dimensional space (or one or more transmitters on the medical device can transmit to reference receivers in the procedure room). Other localization systems, for example using ultrasound, or electric potential, could be used.

Once the points $x_1$, $x_2$, $x_3$, and $x_4$ are identified in three-dimensional space, the points can be processed to determine the configuration of the distal end of the medical device. This processing can determine whether the point $x_1$ is in fact the support point and pivot point of the medical device. For example in a uniform medical device, such as a uniform wall catheter, the distal end portion of the medical device, i.e. the portion distal to the pivot point will assume a generally circular shape. Thus, whether a selected point $x_1$ is in fact the support point or pivot point can be determined by checking the circularity of the reconstructed curve between the points $x_1$, $x_2$, $x_3$, and $x_4$. With other catheter configurations in which the properties are not uniform along the length, the validity of $x_1$ as the support point or pivot point can be determined by checking the shape of the distal end portion against a calculated or empirically determined shape.

In this preferred embodiment, if the point $x_1$ selected as the tentative pivot point or support point, is determined not to be a valid pivot point or support point, the fact is signaled to the user, for example with a text message or by changing the color of the point on the display to signal the user to select another tentative pivot point or support point. Through appropriate processing the system can even suggest one or more appropriate pivot or support points for the user to simply accept. Once the pivot or support point is correctly determined, the processor can then determine the free length l of the medical device that is distal to the pivot or support point.

With the pivot or support point $x_1$, the free length l, and the properties of the distal end portion, as indicated by the positions of the points $x_1$, $x_2$, $x_3$, and $x_4$ identified by the user when a known magnetic field was applied, it is possible to calculate the configuration of the distal end portion of the medical device when a different magnetic field is applied. These calculations can take into account the properties of the medical device as represented in a lookup table or in one or more equations, developed by mathematical modeling or experimental measurements. These calculations can also take into account previous sets of points $x_1$, $x_2$, $x_3$, and $x_4$ identified by the user for the same (or even similar) medical devices.

Thus, it is possible to display a representation 106 of a virtual medical device representing the configuration (shape and orientation) of the actual device if a different magnetic field were applied. (Of course, for other remotely controllable medical devices, the interface would display a representation of a virtual medical device representing the configuration of the actual device as if the control parameter(s) were changed as selected by the user). This representation can be superimposed over the images of the operating region in panes 92 and 94. Thus, the user can select a desired new magnetic field, and then see the configuration of the distal end of the medical device as if the new field were applied, before the new field is applied, and make appropriate adjustments. A variety of systems and methods have been devised for identifying the desired direction of the applied magnetic field. For example, the user can identify the starting point and the ending point (for example on displays of a bi-plane imaging system), and the field can be applied in the selected direction. Alternatively, the user could manipulate a vector representation of the desired field direction, or select previously used directions, or select directions associated with previously identified points (with other remotely controllable medical devices the user can manipulate appropriate control parameters to change the configuration of the device). However, in each case the resulting configuration of the medical device was merely a conjecture of the user, based upon experience. With the present method a display of the configuration that the distal end of the medical device should assume when the desired field is applied can be made before the field is actually applied.

Figure 3A:
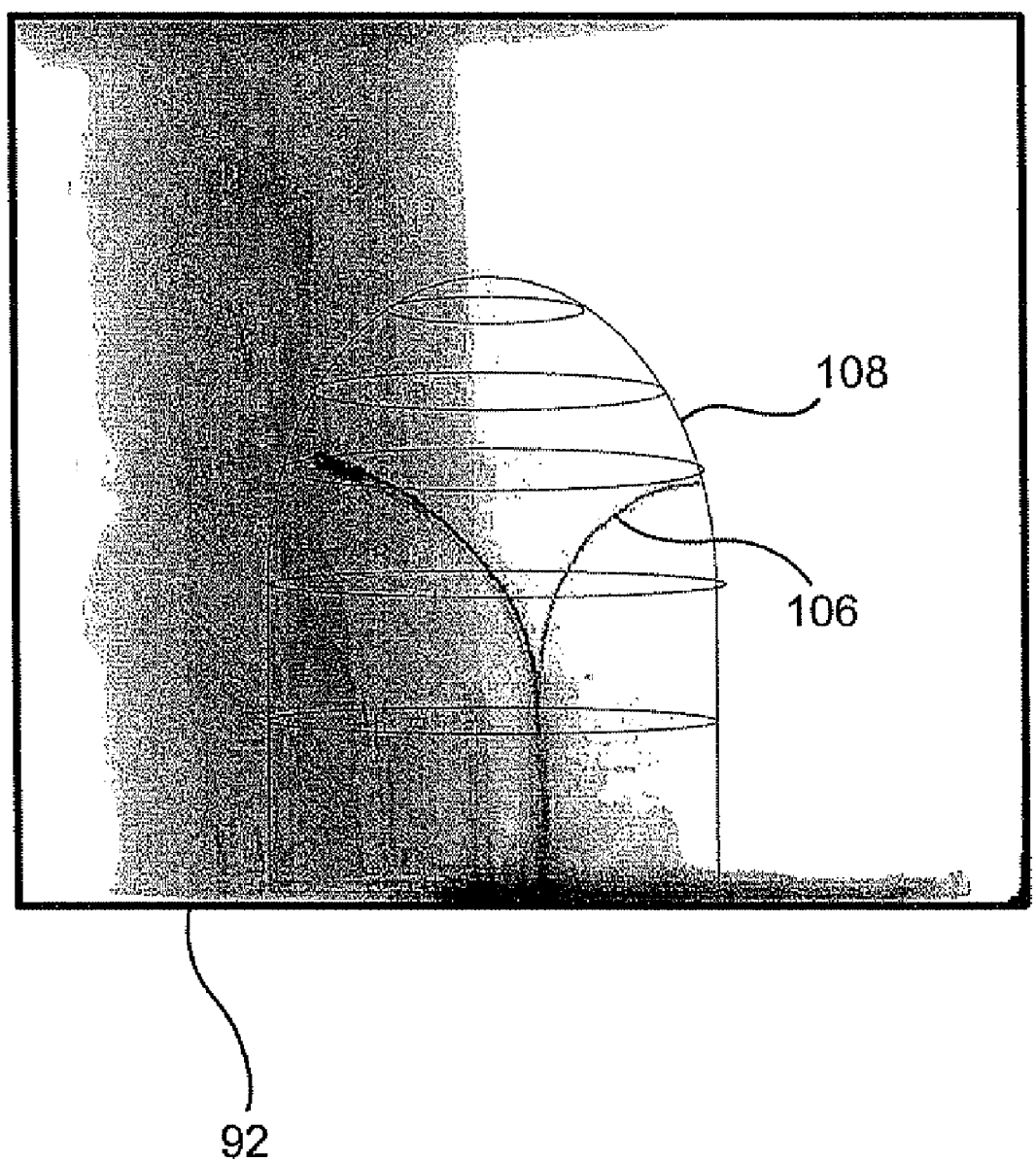
FIG. 3A is an enlarged view of one of the bi-plane imaging displays from the interface shown in FIG. 2, showing a surface of possible positions for the distal end portion of the medical device.
Figure 3B:
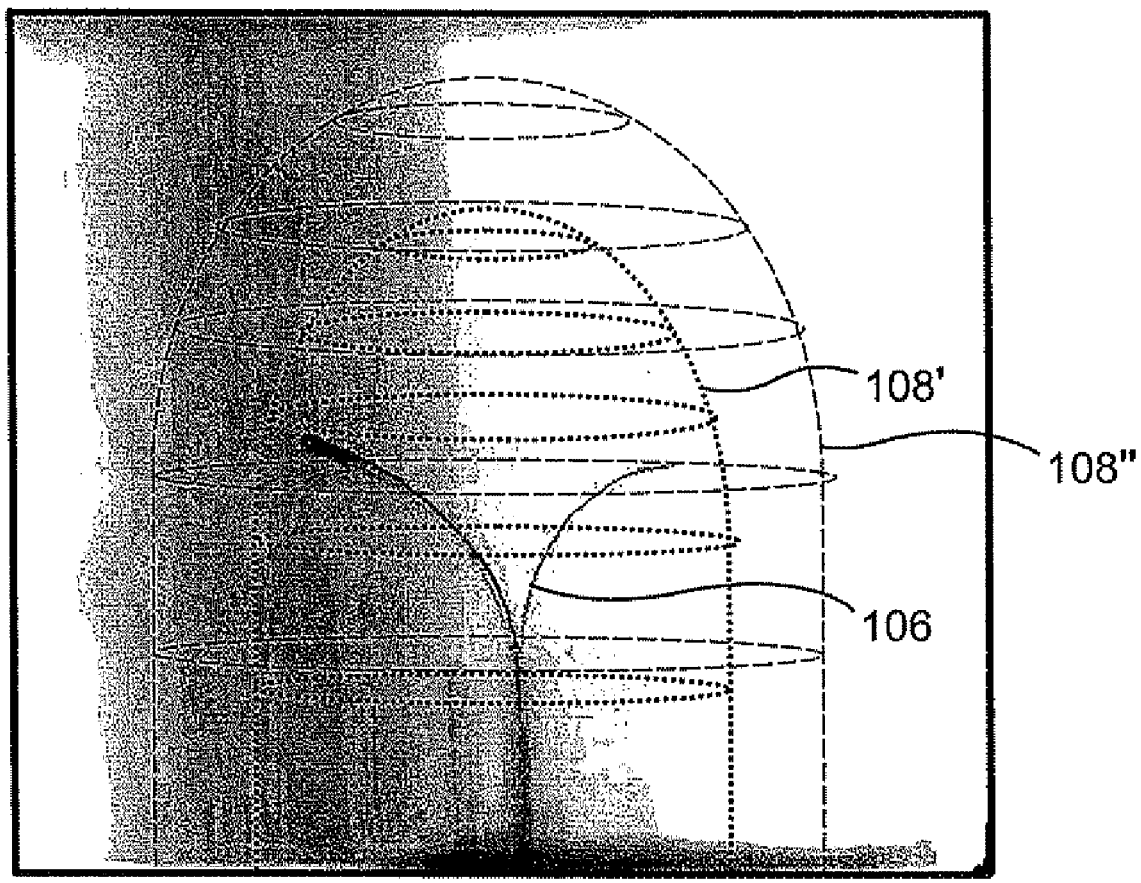
FIG. 3B is an enlarged view of one of the bi-plane imaging displays from the interface shown in FIG. 2, showing surfaces of possible positions for the distal end portion of the medical device for different free lengths l.

Furthermore, as shown in FIG. 3A, it is possible to generate a surface 108 representing all the possible points that the distal end of the medical device can reach with only changes to one or more selected control parameters, such as the magnetic field direction and/or intensity. In this preferred embodiment, this surface 108 has a generally parabolic shape. This surface 108 can also be displayed, and the user can identify a point on this surface, and through processing the system can determine the correct field to apply to cause the distal end of the medical device to reach the selected point. The user can orient the device in the desired direction and reach a point slightly beyond the surface by advancing the medical device slightly. As shown in FIG. 3B, the system can even generate and display surfaces 108' and 108" of possible points for different free lengths l' and l", so that if the surface representing the current set of possible points does not reach the desired location, the user can select from a surface of a different set of possible points, and either manually adjust the free length l, or if the system is equipped with a mechanized advancer mechanism, allow the system to automatically adjust the free length l.

Figure 5:
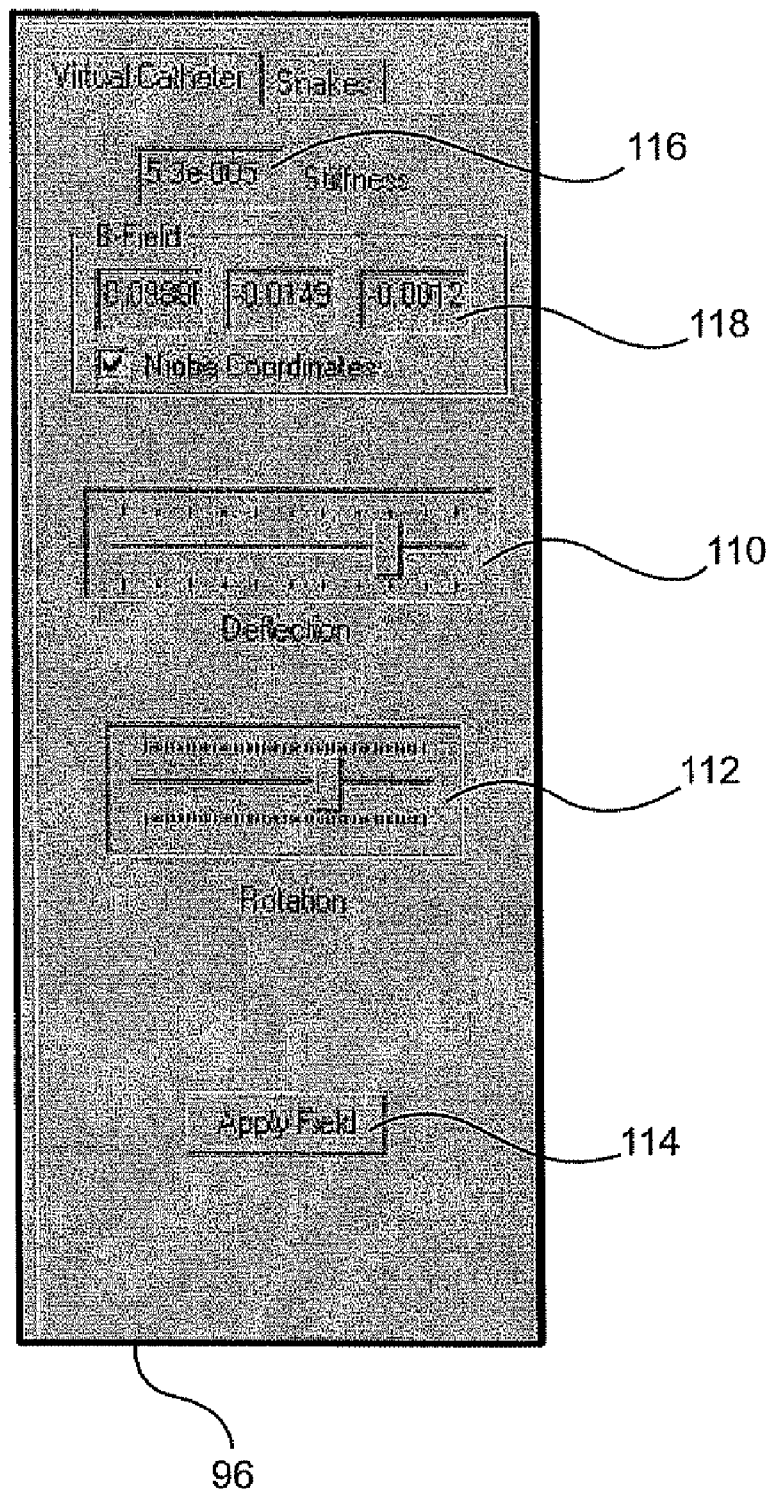
FIG. 5 is an enlarged view of the control panel for the interface shown in FIG. 2.
Figure 6:
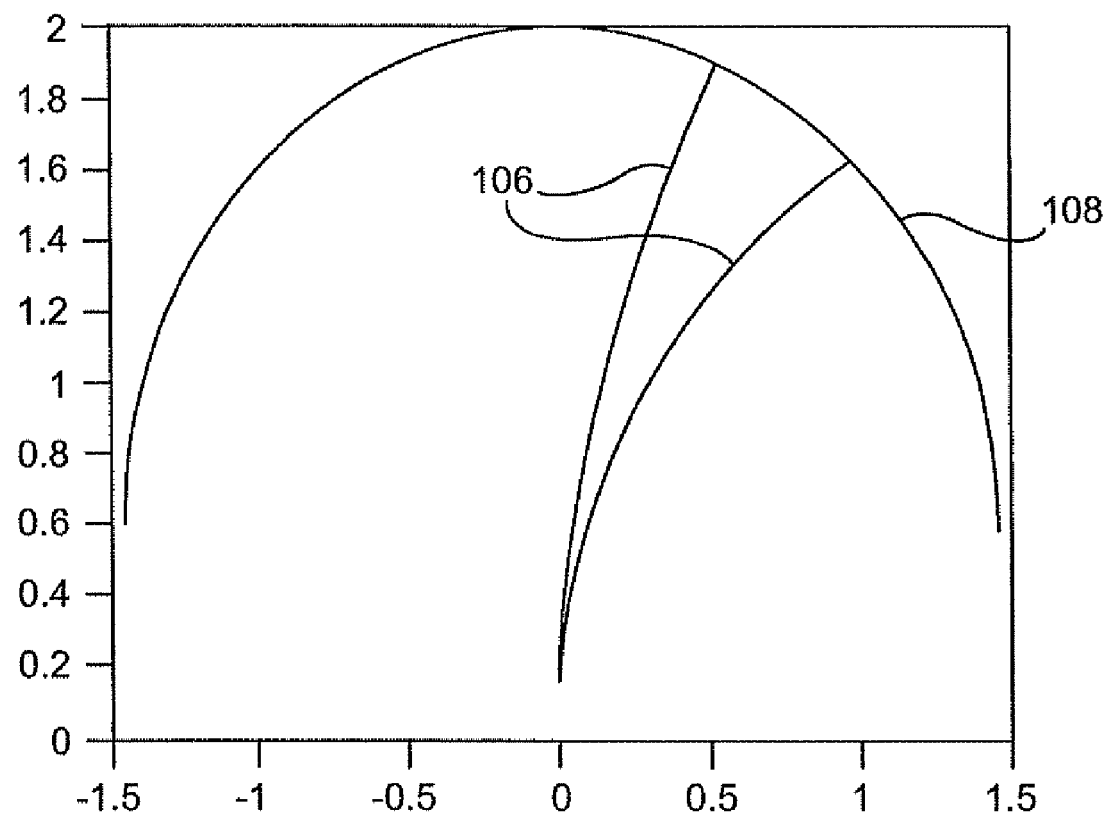
FIG. 6 is a graph showing the points that the fixed length distal end portion of a medical device can contact in a plane.
Figure 7:
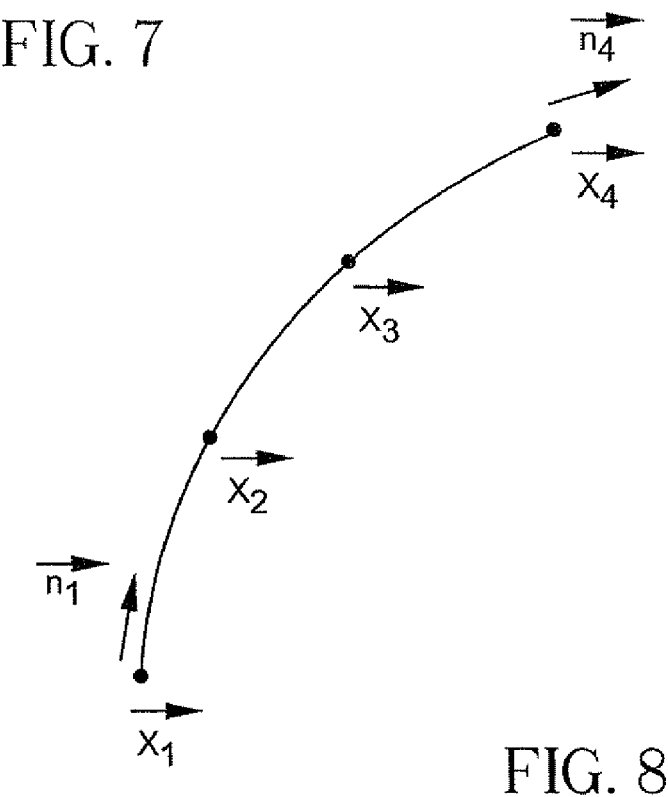
FIG. 7 is a representation of the distal end portion of the medical device, showing points $x_1$, $x_2$, $x_3$, and $x_4$.
Figure 8:
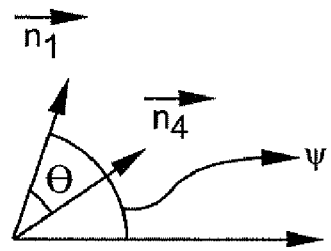
FIG. 8 is a representation of the relation between the direction vectors and the field vector.
Figure 9:
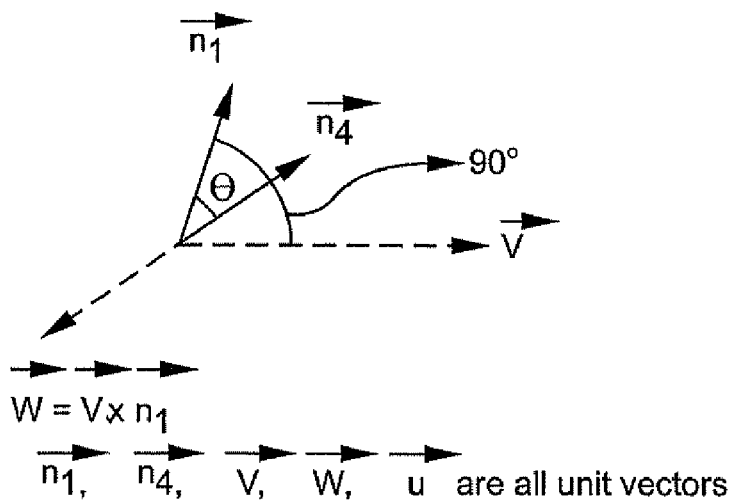
FIG. 9 is a representation of the relation between the direction vectors and $\vec{w}$, the unit vector orthogonal to $\vec{v}$ and $\vec{n}_1$.

The system and method of this invention also allow the user to change the configuration of the displayed representation 106 of the medical device, and apply the field to achieve the desired configuration. Thus the display can be coupled with controls that change the configuration of the displayed virtual image 106 of the distal end portion of the medical device. These controls, can be for example, controls that change the deflection and rotation of the distal end of the device. As shown in FIG. 5, these controls may be implemented by screen controls 110 and 112, which can be operated by pointing, clicking and dragging the control to change the degree of deflection and to change the degree of rotation. These controls 110 and 112 are similar to the controls provided on conventional mechanically navigable devices. In fact, rather than being implemented on the screen, the controls could be provided in a catheter handle, similar to conventional catheter handles, which the user can manipulate to change the deflection and rotation of the distal end of the medical device. Once a desired deflection and rotation are achieved using controls 110 and 112, as indicated by the display of the virtual device in panes 92 and 94, the user can apply the appropriate field, for example by pointing and clicking on a virtual button 114 (or other control), to apply the magnetic field. Alternatively, the system can operate in a continuous mode, in which the configuration of the distal end portion of the medical automatically changes upon a change in the displayed image 106, without the need to operate button 114). The possible configurations of the displayed virtual device are preferably limited to configurations which can be achieved with possible applied magnetic fields, so that user cannot manipulate the virtual device into a configuration that cannot be achieved. This could be built into the controls as well, so that the controls will not allow the user to manipulate the image 106 of the virtual device into a configuration that cannot be physically achieved.

Just as the processor can determine the configuration for a given applied field, the processor can determine the appropriate applied field for a given configuration. Thus the user can specify a configuration, or more preferably a target point, and the interface can determine the control parameters (e.g., magnetic field direction, magnetic field strength, and free length) to reach the target. The interface displays the hypothetical new configuration and if satisfactory, the user can accept it, and the interface-determined control parameter applied to reach the target.

The system can store the properties of various types of medical devices, and one of these stored values could be used in the mathematical model that determines the shape of the display 106 of the virtual medical device. The user can select some of these stored values, and as shown in FIG. 5, the pane 96 can also include a window 116 to display indicia identifying the stored values being used. The pane can also include displays 118 of the magnetic field direction currently being applied.

The interface employs some model of the medical device. The following description illustrates a model in the simple case of a flexible device with uniform elastic properties and with a single permanent magnet located at the device tip. The model and details generalize in a manner that may be determined by those skilled in the art to the case when non-uniform elastic properties and more than one magnet are employed, or when alternative modes of device actuation are used. Mathematically, the configuration of the medical device can be represented as follows:

The distances between the points $x_1$, $x_2$, $x_3$, and $x_4$, are given as follows:

$$d_1 = |\vec{x}_2 - \vec{x}_1| \quad [1]$$

$$d_2 = |\vec{x}_3 - \vec{x}_2| \quad [2]$$

$$d_3 = |\vec{x}_4 - \vec{x}_3| \quad [3]$$

The unit tangent vectors at points $x_1$ and $x_4$ ($\vec{n}_1$ and $\vec{n}_4$) may be estimated as follows:

$$\vec{t}_1 = \frac{(\vec{x}_2 - \vec{x}_1)}{d_1} \quad [4]$$

$$\vec{t}_2 = \frac{(\vec{x}_3 - \vec{x}_2)}{d_2} \quad [5]$$

$$\vec{t}_3 = \frac{(\vec{x}_4 - \vec{x}_3)}{d_3} \quad [6]$$

$$\vec{n}_4' = \vec{t}_3 + \frac{(\vec{t}_3 - \vec{t}_2)}{d_2} \cdot d_3 \quad [7]$$

$$n_4 = \frac{\vec{n}_4'}{|\vec{n}_4'|} \quad [8]$$

$$\vec{n}_1' = \vec{t}_2 + \frac{(\vec{t}_3 - \vec{t}_2)}{d_2} \cdot d_1 \quad [9]$$

$$n_1 = \frac{\vec{n}_1'}{|\vec{n}_1'|} \quad [10]$$

θ, the deformation angle between $x_1$ and $x_4$, can be found from $\cos \theta = \vec{n}_1 \cdot \vec{n}_4$.

Deviation from Planarity

The points $x_1$, $x_2$, $x_3$, and $x_4$ can be checked to make sure that they fall generally in a plane. $\vec{p}$ the unit vector between $x_1$ and $x_4$ is:

$$\vec{p} = (\vec{x}_4 - \vec{x}_1)/|\vec{x}_4 - \vec{x}_1| \quad [11]$$

Then $\vec{q}_1$, a vector orthogonal to $\vec{n}_1$ and $\vec{n}_4$, is given by:

$$\vec{q}_1 = \vec{n}_1 \times \vec{n}_4 \quad [12]$$

and $\vec{q}_2$, a vector orthogonal to $\vec{n}_1$ and $\vec{p}$, is given by:

$$\vec{q}_2 = \vec{n}_1 \times \vec{p} \quad [13]$$

The angle $\phi$ between $\vec{q}_1$ and $\vec{q}_2$ is a measure of the planarity of the points, is given by:

$$\phi = \cos^{-1}(\vec{q}_1 \cdot \vec{q}_2) \quad [14]$$

For planarity it is desirable that $\phi \leq 10° \approx \pi/20$

Circularity Check (Uniform Stiffness)

For a medical device of uniform stiffness, the distal end portion will generally assume a circular configuration. The selection of the points, and particularly the pivot point $x_1$ can be validated by ensuing that they lie substantially along a circle. (For not uniform devices, some other check can be performed on the points). Letting $\vec{u}$ represent the field direction unit vector and defining $\psi = \cos^{-1}(\vec{u} \cdot \vec{n}_1)$, then $\alpha$, the lag angle between the applied magnetic field and the direction of the is given by and define $\alpha \equiv (\psi - \theta)$. If m is the magnetic moment of the magnet on the distal end of the medical device, and $\beta$ its stiffness ($\beta$=EI where E is the Young's modulus of the material and I is the bending moment of area), then:

$$l = \frac{\beta}{mB} \cdot \frac{\theta}{\sin \alpha} \quad [15]$$

where B is the magnitude of the field strength and l is the length of the medical device between $\vec{x}_1$ and $\vec{x}_4$.

The chord length is given by:

$$d' = \frac{2l}{\theta} \sin \frac{\theta}{2} \quad [16]$$

If the points lie along a circle, the chord length d' should be close to $c \equiv |\vec{x}_4 - \vec{x}_1|$, for example, within ten percent, or $$\frac{|c - d'|}{c} \leq 0.1.$$

If the above constraints are satisfied, the curve of the medical device can be estimated as follows:

v, the unit vector in the plane of the medical device orthogonal to $\vec{n}_1$:

$$\vec{v}' = \vec{n}_4 - \vec{n}_1 \cos \theta \quad [17]$$

$$\vec{v} = \vec{v}'/|\vec{v}'| \quad [18]$$

The curve of the medical device is defined by:

$$\vec{x}' = \vec{x}_1 + \frac{l}{\theta}(1 - \cos \theta')\vec{v} + \frac{l}{\theta}\sin \theta' \vec{n}_1 \quad [19]$$

for $0 \leq \theta' \leq \theta$

The envelope or surface of the tip as field direction varies can be determined, based upon the following formula for tip position:

$$\vec{x}_{tip} = \vec{x}_1 + \frac{l}{\theta}(1 - \cos \theta)\vec{v} + \frac{l}{\theta}\sin \theta \vec{n}_1 \quad [20]$$

Varying $\theta$ from 0 to $\theta_{mas}$ (=lMB/$\beta$) gives the envelope or locus of tip positions as the field is varied.

Determining the Field Direction for a Selected Point

If a point Z is selected on the envelope, the field direction that take the tip to that location may be computed as follows:

$$\vec{u}_1 = \frac{(\vec{z} - \vec{x}_1)}{|\vec{z} - \vec{x}_1|} \quad [21]$$

$$\overline{\phi} = \cos^{-1}(\vec{u}_1 \cdot \vec{n}_1) \quad [22]$$

$$\overline{\theta} = \cot^{-1}\left[\frac{(1 - \tan^2 \overline{\phi})}{2 \tan \overline{\phi}}\right] = 2\overline{\phi} \quad [23]$$

$$\overline{\psi} = \overline{\theta} + \sin^{-1}\left(\frac{\beta \overline{\theta}}{MBl}\right) \quad [24]$$

Then the corresponding field direction to orient the tip to point z is given by the unit vector:

$$\vec{u}_B = \vec{n}_1 \cos \overline{\psi} + \vec{v} \sin \overline{\psi} \quad [25]$$

An "accessible surface" may also be defined by rotating the envelope obtained in equation 25 about $\vec{n}_1$. $\vec{w}$, the unit vector orthogonal to $\vec{v}$ and $\vec{n}_1$, is given by $\vec{w} = \vec{v} \times \vec{n}_1$, and $\vec{v}_R$, the rotation of $\vec{w}$ about $\vec{n}_1$ is given by $\vec{v}_R = \cos \xi \vec{v} + \sin \xi \vec{w}$ for $0 \leq \xi \leq 2\pi$ Then:

$$x_s = x_1 + \frac{l}{\theta}(1 - \cos \theta)(\cos \xi \vec{v} + \sin \xi \vec{w}) + \frac{l}{\theta}\sin \theta \vec{n}_1 \quad [26]$$

defines a surface of revolution about $n_1$ that is the surface accessible to the tip by changing the field direction by varying $\theta$ and $\xi$, a surface is generated analogous to generating a sphere with longitude and latitude.

Generating the Field Direction to any Point on the Surface

As in Equation [25], given a desired point $\vec{z}$ on this surface, a corresponding field direction is obtained from:

$$u_{B,S} = \vec{n}_1 \cos \psi + \vec{v}_{R,S} \sin \psi \quad [27]$$

where $\vec{v}_{R,S}$ is obtained from:

$$\vec{v}_{R,S} = \cos \xi_s \vec{v} + \sin \xi_s \vec{w} \quad [28]$$

where $$\xi_s = \tan^{-1}\left(\frac{\vec{u}\cdot\vec{w}}{\vec{u}\cdot\vec{v}}\right) \quad [29]$$

When the desired tip location is beyond the accessible surface, then a combination of change of inserted length and field direction is needed to move the distal end of the device to $\vec{z}$ from its current location.

As before, define $\vec{u}_1$, and find $\bar{\phi}$ and $\bar{\theta}$. If $\bar{l}$ is the new medical device length, and $$y = (\vec{z}-\vec{x}_1)\cdot\vec{n}_1, \text{ then } \bar{l}\frac{\sin\bar{\theta}}{\bar{\theta}} = y \text{ or } \bar{l} = \frac{y\bar{\theta}}{\sin\bar{\theta}}. \quad [30]$$

$$\bar{\psi} \equiv \bar{\theta} + \sin^{-1}\left(\frac{\beta\bar{\theta}}{MB\bar{l}}\right)$$

Given Equations 28 and 29:

$$\vec{u}_{B,S} = \vec{n}_1 \cos\bar{\psi} + \vec{v}_{R,S}\sin\bar{\psi} \quad [31]$$

and $$\delta l = (\bar{l}-l) \quad [32]$$

is the change in inserted length which together with the change in field direction will take the end of the medical device to the desired location.

Of course, while described herein in the context of controlling a magnetic surgery system, as stated earlier the virtual device interface of this invention could be applied to other systems which can control the configuration of medical device, including devices whose configuration is controlled mechanically, hydraulically, or through magnetostrictive and electrostrictive means.

Figure 10:
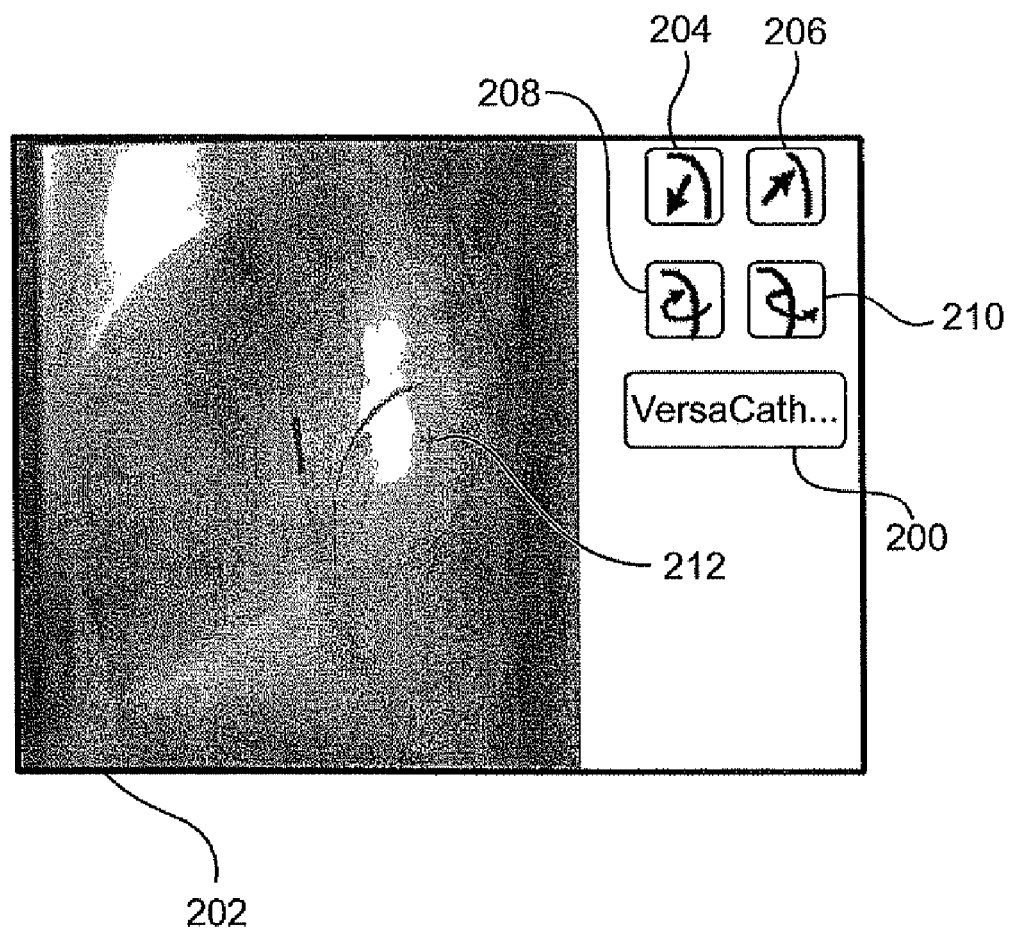
FIG. 10 is representation of a display for an alternate display for a second embodiment of a user interface, that selectively employs a virtual medical device display.

A second embodiment of user interface is illustrated in FIG. 10. The interface of the second embodiment is adapted to help a user control a magnetic navigation system that applies a magnetic field to an operating region in a patient to control the direction of a magnetic medical device in the operating region. An advancer/retractor mechanism is preferably also provided for the controlled advancement/retraction of the medical device. As shown in FIG. 10, the user is presented an interface with several virtual or real buttons, which the user can operate using a mouse, track ball, space ball, joy stick, tablet, or other input device. Operating button 200 initiates the navigation under the present invention, and a window (or other message) is displayed, prompting the user to use the input device to identify a number of points on the medical device on the display 202, including an image 203 of the medical device including the anchor point.

The user identifies points, for example, by positioning the cursor over the medical device on the display 202. In this preferred embodiment, the inventors have determined that four points is an appropriate balance between user effort and accuracy in characterizing the medical device to be navigated, but other numbers of points could also be used. The points identified are checked or qualified (as described above) and a window (or other message) alerts the user if one or more points are not properly identified.

With information about the currently applied magnetic field and the position and configuration of the medical device (resulting from the identification of points), the processor implementing the interface can characterize the medical device. The user can then use the input device to operate direction control buttons. In this preferred embodiment there are four such buttons, buttons 204 and 206 for increasing and decreasing the deflection of the medical device, and buttons 208 and 210 for rotating the medical device. The interface can be operated in a discrete navigation mode, a continuous navigation mode, or the interface can allow the user to switch between discrete and continuous navigation. In the discrete navigation mode the user clicks on the buttons 204, 206, 208, or 210, and the image 212 of the a virtual device is superposed over the display 202 showing the configuration of the medical device with the specified new magnetic field applied. Once the user is satisfied with the new field, as represented by the image 212 of the virtual device, then the user operates a control (such as a button) to activate the magnetic navigation system and apply the specified field, causing the actual medical device to assume substantially the configuration and position represented by the image 212 of the virtual device. In the continuous navigation mode, the user could operate in a continuous navigation mode, changes in the direction specified by operating buttons 204, 206, 208, and 210 are automatically implemented, moving the medical device. The user may enter the continuous navigation mode, for example, by holding down a control button. The buttons 204, 206, 208, and 210 preferably can be operated to change deflection and rotation in predetermined, discrete amounts, which preferably can be customized by the user, or can be held down to continuously change the deflection and rotation to the limits of the navigation system. Many other mappings besides separate control of rotation and deflection of the device are possible. For example, the device tip could be controlled or actuated suitably to move within a chosen plane.

In another embodiment a joystick is provided for interactive device control purposes. In this case, the user would select from a set of possible mappings from joystick deflections to changes in actuation control variables that would modify the configuration of the device. In one particular case where a magnetic surgery system is used for device actuation, the magnetic field would be driven from the joystick. Visual feedback from an imaging system that could employ X-ray, Magnetic Resonance Imaging, Ultrasound or other imaging modalities known to practitioners of the art provides the user with the device configuration, so that the device may be driven interactively by the user to reach a desired target. Other embodiments may use spaceballs or a variety of other input devices, including those that are custom-built, for interactive remote control of device actuation.

The interface also allows the user to click on a point in the display to mark a target point 214 on the two dimensional display. The interface then determines the magnetic field required of the magnetic navigation system and extension or retraction of the medical device (which is preferably controlled by an automated advancing/retracting system) required to reach the target point 214, and displays an image 216 of a virtual device with the calculated magnetic field applied, and with the appropriate adjustment in length made. The user then operates a control (such as a button), so that calculated field and adjustments in length are applied. Alternatively, the user could operate in a continuous navigation mode (such as by holding down another button on a joystick) so that the applied magnetic field and device length automatically change to bring the distal end of the medical device to the point 214 identified by clicking on the display 202.

Because the user is attempting to identify a point in three dimensional space by identifying a point on a two dimensional display, the distal end of the medical device may not be precisely where the user intended. The user can switch to another display (if biplane imaging of the operating region is available) to refine the position. Alternatively, where biplane imaging or two corresponding images are available, the user can identify the target point on each image, uniquely identifying the point in three dimensional space. After the user identifies the target in one image, the interface assists the selection of a proper point in the second image. For example, the cursor color or shape can indicate when the cursor is over a valid or invalid position based upon the user's selection on the other display. In discrete navigation, the magnetic navigation system applies the required field to achieve the specified target point when the user actuates an apply field button. In one embodiment of continuous navigation, the magnetic navigation system automatically begins to apply the required field to achieve the specified target point as soon as the target point is properly specified. To prevent unintended movement, the user preferably has to hold down a button to remain in the continuous navigation mode, and when the button is released the magnetic navigation system ceases movement. In an embodiment that employs a joystick, for example, the button could be a trigger button on the joystick. In practice, the apply field button used in the discrete navigation mode and the continuous navigation button used in the continuous navigation mode can be the same.

Alternatively, the user can make minor adjustments to the position using the buttons 204, 206, 208, and 210. Once the medical device is characterized, as prompted by the interface system, the system can automatically interpret further pointing and clicking on the display 202 as an indication that the user is identifying a target point 214. Alternatively, a button can be provided on the display or on the input device for the user to turn on the target mode.

As mentioned previously, rather than buttons 204, 206, 208, and 210, the user can input directional changes with a joystick. For example, moving the joystick forward and backward can increase and decrease the deflection, and moving the joystick left and right (or twisting the joystick) can cause rotation. Likewise, it is possible to employ other modes of mapping from the joystick to device actuation. As with using the buttons above, the user can operate in discrete or continuous mode. When operating in discrete mode, the user uses the joystick to position a virtual image 212 on the display 202, and when satisfied with the position, operates a control (such as a button on the joy stick) to cause the navigation system to apply the magnetic field. When operating in the continuous mode, the user operates a control (such as holding down a button on the joystick) so that changes indicated by the movement of the joystick are automatically implemented, with the magnetic navigation system moving in response to change the fields as required. In this mode the medical device responds interactively as the user operates the joystick.

In a preferred embodiment, advancement of the medical device is preferably separately controlled by the user, for example with a toggle switch on the joystick so that a single joystick can be used for both device steering and device advancement or retraction, or with a separate button on the display 202. However in the target mode, the interface preferably controls both the magnetic navigation system and the advancer system, so that the device is directly computer controlled. In yet another preferred embodiment, advancement of the medical device and device deflections or shape changes are controlled by the user from separate joysticks. Various other embodiments and modes of use may be conceived by those skilled in the art.

Figure 11:
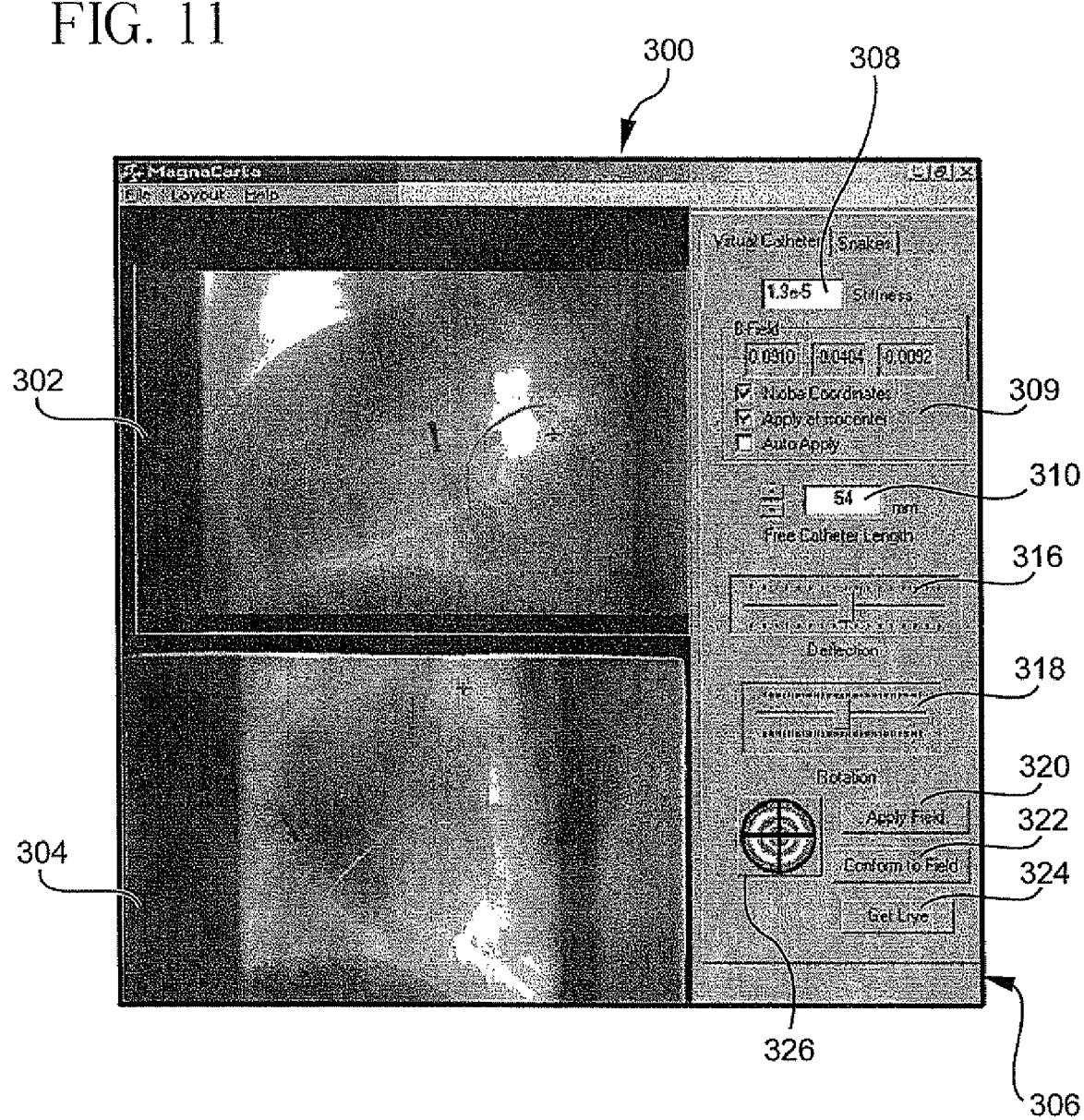
FIG. 11 is a representation of an alternate display for a second embodiment of a user interface that selectively employs a virtual medical device display.

FIG. 11 shows a display 300 from another implementation of the interface system of the second embodiment. The display 300 includes two bi-plane images 302 and 304 of the operating region. The display also includes a control pane 306. The control pane may include a box 308 in which the user can select or specify the stiffness of the medical device; alternatively the medical device type may be selected from a menu of medical devices whose stiffness value is pre-programmed into the system. A computer processor can use the stiffness to determine the configuration of the medical device in an applied magnetic field, both to generate virtual images of the device under specified magnetic fields, and to calculate the applied field to reach a particular target point.

The control pane 306 also includes a field display 309, with the coordinates of the current magnetic field direction, and pick boxes for selecting the point of application of the field. The control pane has free length box 310, which allows the user to select the free length of the medical device from the end of its sheath. Arrows 312 and 314 allow the user to increase and decrease the specified length, which is implemented by an advancer/retractor mechanism. The control pane 306 also includes slide controls 316 and 318 for controlling the degree of deflection and rotation (like buttons 204 206, 208 and 210). An apply field button 320 allows the user to apply the field specified by the virtual device in the displays. A conform to field button 322 causes the virtual device model to predict and show the shape that would be caused by application of an input magnetic field. A get live button 324 updates the images 302 and 304. Finally, a target mode button 326 allows the user to enter the target mode (as described above), so that pointing and clicking on the displays 302 and 304 identifies a point which the virtual medical device moves to in the discrete mode, or which the actual medical device moves in the continuous mode.

Figure 12:
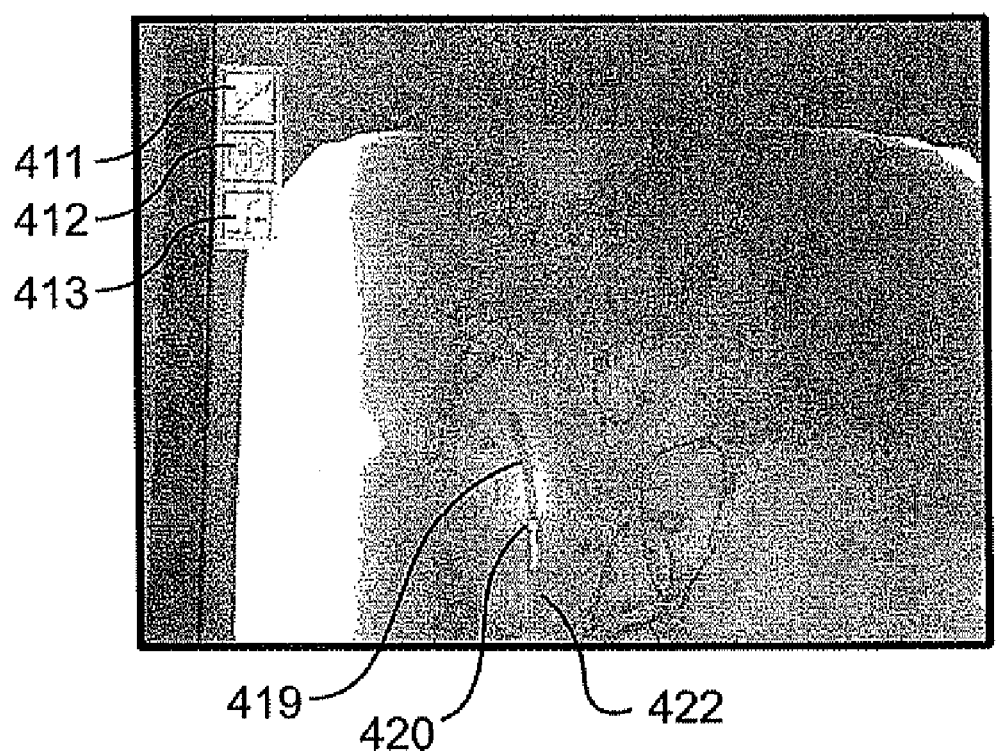
FIG. 12 is a representation of a display from a third embodiment of a user interface, with screen buttons.
Figure 13:
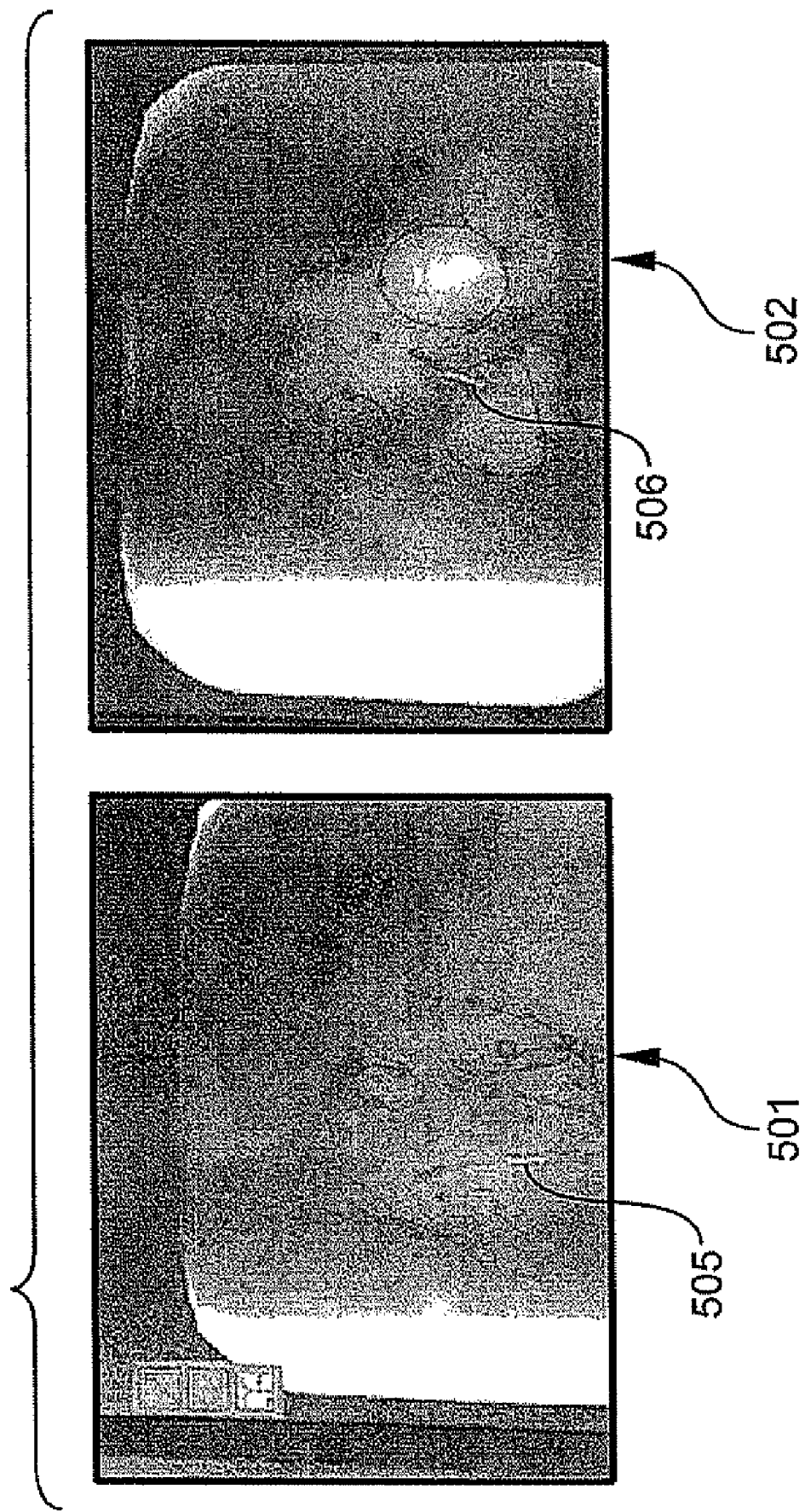
FIG. 13 is a representation of the LAO and RAO images from the third embodiment of the user interface.
Figure 14:
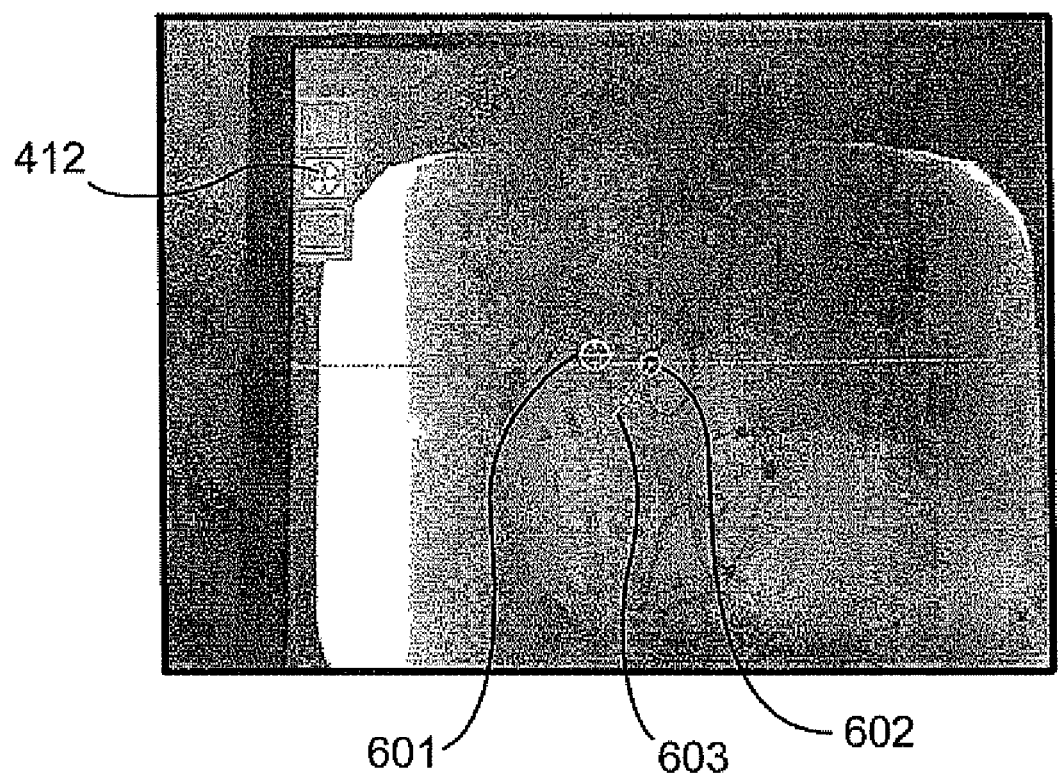
FIG. 14 is a representation of the RAO image of the third embodiment of the user interface in target mode, showing the target cursor, the target, and the virtual device.

In still another embodiment of user interface according to the principles of this invention, the user interaction can be simplified further for ease of use. In FIG. 12, graphical buttons 411 and 412 are provided as alternate modes of control of a magnetic navigation system. Button 411 when selected enables defining the direction of the magnetic field in three dimensional space by specification of the direction in two projections (commonly the LAO and RAO perspectives familiar to interventional surgeons). When the corresponding magnetic field is applied to steer a medical device, the device tends to align itself with the magnetic field but with a certain angular lag as dictated by the elastic and magnetic properties of the device. In contrast, button 412 enables direct selection of a target location that the device can move to. In order to use this mode, the user first selects a "Mark catheter base" button 413 (shown highlighted in FIG. 12) with a mouse click. This enables the user to indicate (by drawing with a pen-tablet or by suitably dragging a mouse) the pivot or point of support of the device as well as the pivot direction, by suitably drawing a line in two projected X-ray views. In FIG. 12, a catheter 419 can be seen to extend from a guide sheath 422. The line 420 drawn by the user indicates the pivot point to be the distal tip of the sheath and the direction in which the device 419 is extended at the pivot point. FIG. 13 shows the pivot point and direction marked by lines 505 and 506 respectively in RAO and LAO views 501 and 502. This process in effect provides $x_1$ and $n_1$ to the system. Next the user selects the target button 412 as shown in FIG. 14. This provides to the user a "Target" cursor 601 that enables selection of a point 602 in three dimensional space from two X-ray projections. This point is the desired anatomical target point that the user wishes to steer the medical device to. The computer then calculates the requisite field direction and insertion length from equations

Figure 15:
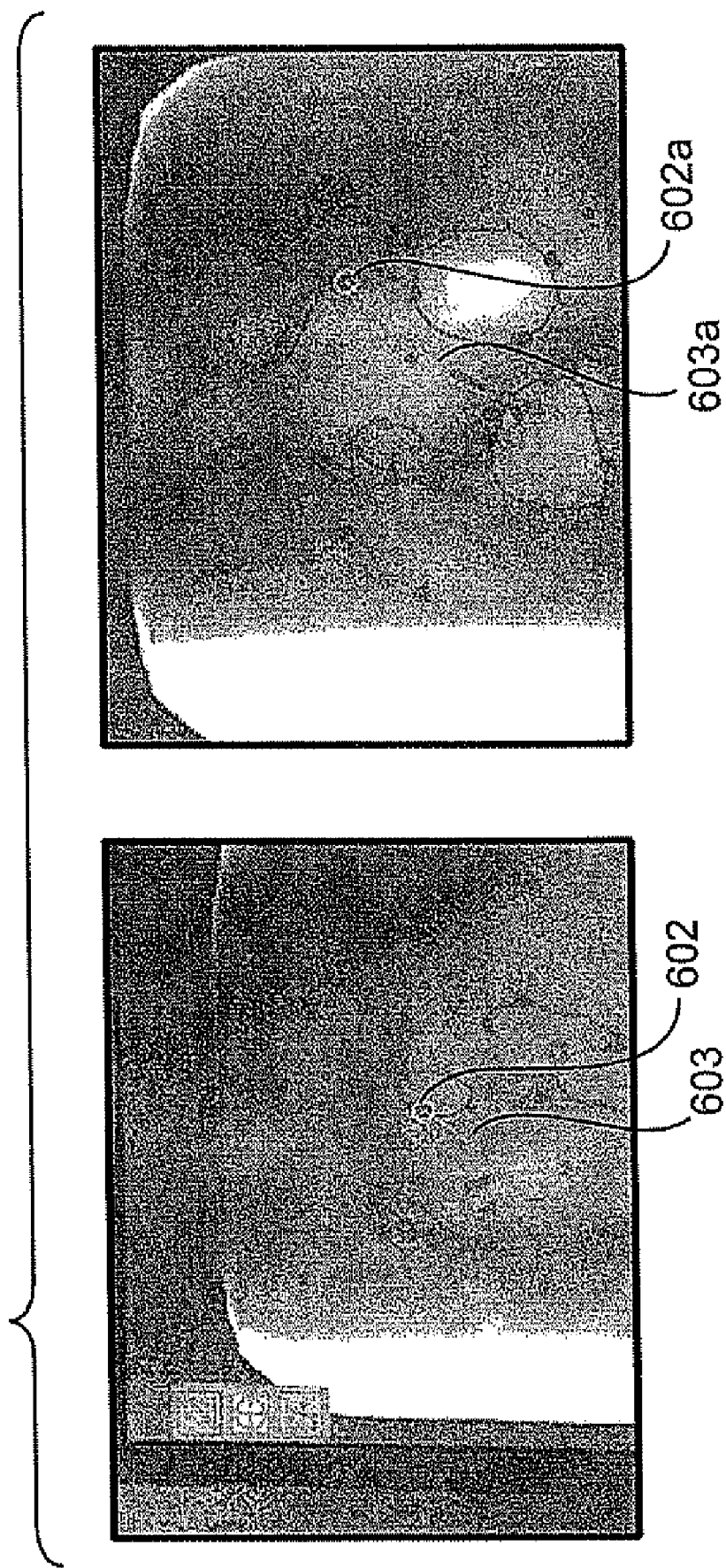
FIG. 15 is representation of the LAO and RAO images from the third embodiment of the user interface in target mode, showing the virtual device extending to a selected target.

(25) and (32). The corresponding shape of the device is also computed and displayed as a dashed curve 603. FIG. 15 shows a desired target point in RAO and LAO projections respectively as 602 and 602a together with associated projections of the device shape 603 and 603a11 respectively.

Figure 16:
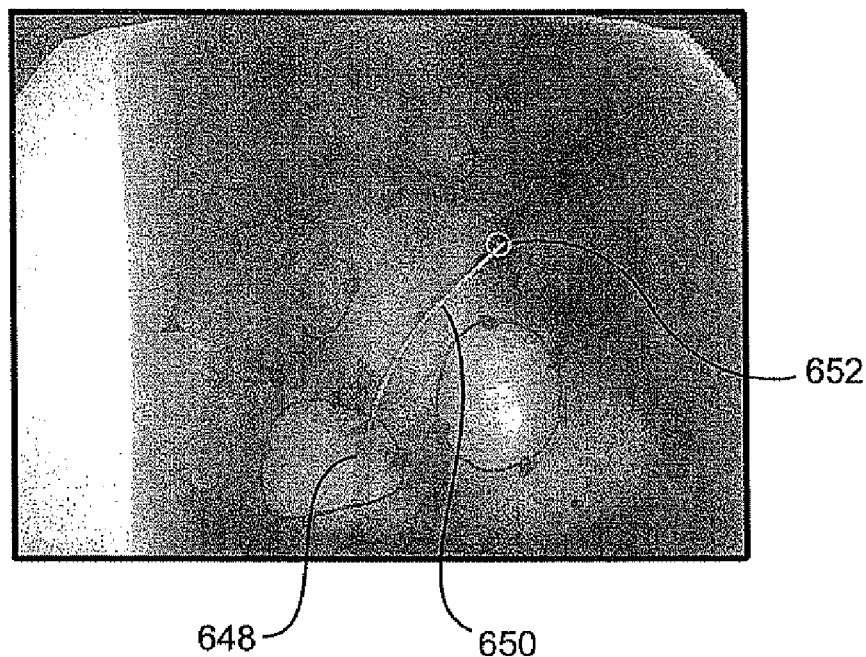
FIG. 16 is a representation of the LAO image of third embodiment of the user interface, showing the virtual device after the change in control has been effected.
Figure 17:
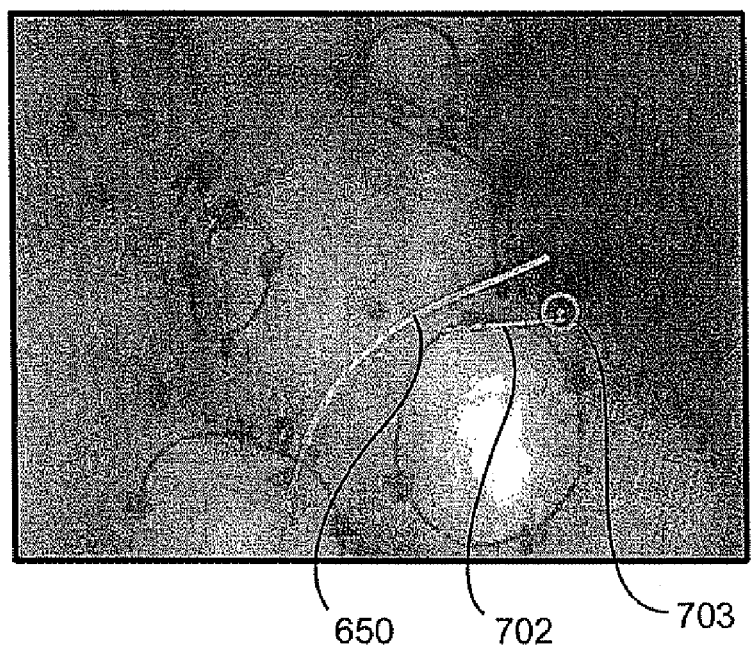
FIG. 17 is a representation of the LAO image of the third embodiment of the user interface, showing a further change in the virtual device after a prior change in control has been affected.

The required field direction and insertion length may be automatically applied by the system upon the press of a button. Alternatively, the field direction may be applied directly by the system while the user continuously controls the advancement or retraction of the device. The device curve may be updated to be shown as a solid curve, perhaps in a different color, to indicate that the desired change of controls has been effected. FIG. 16 shows an LAO perspective of such an updated device curve 650 together with the user-defined pivot direction 648 and the desired target location 652. Further the device shape may be interactively manipulated by the user as described above. One convenient implementation uses keyboard buttons for increasing or decreasing deflection of the virtual device and for rotating it clockwise or anti-clockwise about the pivot direction. The device shape is continuously computed and updated in the projected displays as well as possibly in a three dimensional display during this process of user adjustment. The corresponding manipulated virtual device 702 is shown in an LAO perspective in FIG. 17 together with the current device configuration 701 and an updated location 703 for the device tip as the use manipulates the virtual device. Once a desired device shape or tip location is achieved the corresponding controls may be applied at the touch of an "Apply" button, or alternatively the system may apply the controls (magnetic field and insertion/retraction in one embodiment) in user-defined steps every time a keyboard button is pressed. Another convenient implementation of continuous control uses a joystick or other input device together with a mapping function to convert joystick movements to changes in control inputs, causing the device to respond continuously to joystick movements. In one implementation the user could, together with moving or deflecting the joystick, press and hold a "trigger" button to cause the changes in control inputs to be applied. The user observes (on an X-ray image or other mode of visualization) the device response to joystick movements and may interactively stop device response when a desired device configuration has been attained, for example by releasing a "trigger" button on the joystick.

The actuation system employed to steer or orient the flexible device can take several different forms such as magnetic actuation by external magnetic fields, mechanical actuation through the use of steering cables or other force transmission elements within the device, device actuation using piezoelectric materials or electrostrictive polymers such as silicone elastomers, actuation with magnetostrictive elements embedded in the device, or other technologies known to practitioners of the art.

In a preferred embodiment, the actuation system can use magnetic fields generated by external magnets to orient magnets incorporated in the distal portion of the device. The interaction of the external field with the device magnets serves to orient the device in controllable fashion by controlling the externally applied magnetic field. The external magnets could employ either permanent magnets or electromagnets possibly employing superconductivity to produce strong magnetic fields. FIG. 1 shows a schematic illustration of such a system and device.

Figure 18:
FIG. 18 is a side elevation view of a medical device constructed according to the principles of this invention, and adapted for control by various embodiments of this invention.

In an alternate preferred embodiment employing electrostrictive actuation, the device could use electrically activated electrostrictive materials to bend or steer the device. FIG. 18 shows a flexible device 851 which incorporates electrostrictive elements 854 and 855. Electrical leads 858, 859 and 865, 866 connect the elements 854 and 855 respectively to a voltage source 856. The electrostrictive element 854 is sandwiched between rings 860 and 862. When a voltage is applied across the leads 858 and 859, the electrostrictive element 854 decreases in length, forcing the flexible device to bend in the plane defined by the device axis and the orientation of the electrostrictive element relative to the device axis. The amount of bending can be controlled by varying the applied voltage. When a voltage is applied across leads 865 and 866, the shortening of element 855 forces the device to bend in the opposite direction.

In some cases, it may be useful to determine the bending plane of the device. This is relevant where a non-magnetic steering mechanism is used to orient the device. This may be done by employing an imaging method such as X-ray imaging or by using a localization sensor embedded in the device. If a localization sensor which gives complete position and orientation of the device is used, the orientation of the actuation mechanism such as steering cable or electrostrictive element is known in a reference configuration, the corresponding orientation in a general configuration may be obtained by processing the data obtained from the localization sensor. Thus the bending plane of the device in three dimensional space may be determined. Alternatively, from imaging such as fluoroscopy, the change in the tangent vector to the device tip upon a small change in an actuation control variable may be recorded, which also provides information needed to determine the bending plane in three dimensional space.

Knowledge of the bending plane can be used to control the device for targeting purposes and for configurational changes with the aid of a computational model in a manner similar to that described above.

The embodiments discussed here are for purposes of example only, and other embodiments of actuation systems such as mechanical actuators or others known in the field can be used for device steering. In the following a computational model for magnetic actuation with externally applied magnetic fields is described as a non-limiting example, with the understanding that the computational model and its use can generally incorporate a variety of possible actuation systems.

The actuation system coordinates may be registered to the imaging system coordinates and to the localization system coordinates by means of several methods known to those skilled in the art. For example, the actuation system may employ external magnetic fields, in which case the source of the fields such as an external magnet could be mechanically registered to the imaging system by the use of suitably placed markers placed in known positions with respect to the actuation system. These positions may also be ascribed coordinates in the reference frame of the imaging system since information from multiple imaging projections or from three dimensional imaging would be available from the imaging system. The positions of three markers determined in both coordinate systems suffices to generate a rigid coordinate transformation (rotation and translation) which is the requisite registration. Additional markers may be used for improved accuracy as desired.

Likewise if a device localization system is used, it could be used to determine the coordinates of known markers with respect to the localization system as well, thence providing a mutual registration of the various distinct coordinate frames employed by the various systems. In practice, such a registration would be performed at the start of a medical procedure. Subsequent movement of the patient table may be tracked to within a suitable accuracy to permit updated registrations as may be required on a regular basis during a clinical procedure.

While a magnetic actuation system has been discussed in the above for non-limiting illustrative purposes, various alternative actuation systems may be deployed and registered as needed according to the methods taught here. For example, a device employing piezoelectric actuators may use a coordinate frame in common with an X-ray imaging system, requiring only registration to a device localization system. Likewise, the markers in question may be either mechanically placed by the user or may be based on anatomical locations as pinpointed by the user.

What is claimed is:

1. A method of operating a navigation system that remotely configures the distal end portion of a medical device inside a subject's body, the method comprising:
    displaying a virtual representation of at least a portion of the medical device, based upon a computational physics-based model of the medical device;
    accepting inputs made by a user to change the configuration of the portion of the medical device represented by the displayed virtual representation, and updating the virtual representation of the portion of the medical device based upon the computational physics-based model; and
    operating the navigation system using the computational physics-based model of the medical device to cause the portion of the medical device to conform to the desired configuration represented by the updated virtual representation.

2. The method according to claim 1 wherein the user makes inputs remotely from the subject.

3. The method according to claim 1 wherein the medical device is an elongate medical device having a proximal end outside the subject's body, and a distal end inside the subject's body, wherein the virtual representation is of at least the distal end portion of the medical device, and wherein the navigation system changes the configuration of at least the distal end portion of the medical device.

4. The method according to claim 3 wherein the step of displaying a virtual representation of the distal end portion of the elongate medical device includes superposing the representation of the end portion of the elongate medical device over a representation of the operating region in the subject.

5. The method according to claim 4 wherein the representation of the operating region in the patient is derived from an x-ray image.

6. The method according to claim 4 wherein the representation of the operating region in the subject is derived from a CT image.

7. The method according to claim 4 wherein the representation of the operating region in the subject is derived from an MR image.

8. The method according to claim 4 wherein the representation of the operating region in the subject is derived from an ultrasound image.

9. The method according to claim 4 wherein the representation of the operating region in the subject is derived from a map of points on surfaces in the operating region.

10. The method according to claim 3 wherein the navigation system operates in response to control variables, and wherein the step of accepting inputs made by a user to change the configuration of the distal end portion of the elongate medical device represented by the displayed virtual representation, comprises accepting desired changes to the control variables of the navigation system, corresponding to desired changes in the operating state of the navigation system, and updating the virtual representation of the distal end portion of the elongate medical device to show the medical device as if the control variables of the navigation system were actually changed.

11. The method according to claim 10 wherein the navigation system comprises at least one external magnet for applying a magnetic field to a magnetically responsive element on the medical device, and wherein the system accepts inputs of desired changes in the magnetic field direction.

12. The method according to claim 3 wherein the step of accepting inputs made by a user to change the configuration of the distal end portion of the elongate medical device represented by the displayed virtual representation, includes accepting input of a new direction for the distal end portion of the elongate medical device.

13. The method according to claim 3 wherein the step of accepting inputs made by a user to change the configuration of the distal end portion of the elongate medical device represented by the displayed virtual representation, includes accepting input of a deflection for the distal end portion of the elongate medical device from its current configuration.

14. The method according to claim 3 wherein accepting inputs made by a user to change the configuration of the distal end portion of the elongate medical device represented by the displayed virtual representation, includes accepting input of a new position for the distal end portion of the elongate medical device.

15. The method according to claim 3 wherein the navigation system comprises elements in the medical device which, when operated, change the configuration of the distal end portion of the medical device.

16. The method according to claim 15 wherein at least some of the elements which change the configuration of the distal end portion of the medical device are electrostrictive elements.

17. The method according to claim 15 wherein at least some of the elements which change the configuration of the distal end portion of the medical device are magnetostrictive elements.

18. The method according to claim 17 further comprising applying a magnetic field from an external source magnet to the magnetostrictive elements change the configuration of the distal end portion of the medical device.

19. The method according to claim 3 wherein the navigation system comprises mechanical links in the medical device which, when translated, change the configuration of the distal end portion of the medical device.

20. The method according to claim 3 wherein the step of operating the navigation system occurs automatically after the inputs by the user are accepted.

21. The method according to claim 3 wherein the step of operating the navigation system only occurs after an input by the user.

22. The method according to claim 3 wherein the computational physics-based model is based at least in part on the physical characteristics of the medical device.

23. The method according to claim 22 wherein the computational physics-based model is based at least in part on a mathematical representation of at least one physical characteristic of the medical device.

24. The method according to claim 22 wherein the computational physics-based model is based at least in part on measurements of at least one physical characteristic of the medical device.

25. The method according to claim 3 wherein the position of the distal end portion of the medical device is controlled by an advancing and retracting mechanism, and wherein the method further comprises accepting inputs made by the user to change the position of the distal end portion of the medical device, and updating the virtual representation of the distal end portion of the elongate medical device; and operating the advancing and retracting mechanism to cause the distal end portion of the elongate medical device to conform to the desired position represented by the updated virtual representation.

26. The method according to claim 3 further comprising determining the actual position and configuration of the distal end portion of the medical device, comparing the actual position and configuration of the distal end portion of the medical device, with the position and configuration given by a computational model to determine the force of contact between the medical device and tissue in the operating region by computational means.

27. A method of operating a navigation system that remotely configures the distal end portion of a flexible medical device inside a subject's body to reach a target, the method comprising:
displaying a representation of the operating region;
accepting an input of the configuration of a portion of the device and displaying a representation of the configuration of said portion;
accepting an input of a target on the display of the operation region;
determining the inputs necessary to the navigation system to cause the medical device to assume a configuration to reach the target based upon a computational physics-based model incorporating properties of the medical device and the navigation system; and
applying the determined inputs to the navigational system to cause the medical device to assume a configuration to reach the target.

28. The method according to claim 27 wherein the medical device is an elongate medical device having a proximal end outside the subject's body, and a distal end inside the subject's body.

29. The method according to claim 28 wherein the navigation system can both change the configuration of the distal end portion of the medical device and advance or retract the distal end of the elongate medical device.

30. The method according to claim 28 wherein the navigation system comprises at least one magnet that applies a magnetic field of selected direction to a magnetically responsive element on the medical device, and wherein determining the inputs necessary to the navigation system to cause the elongate medical device to reach the target based upon a computational model of the elongate medical device and the navigation system includes determining the magnetic field direction needed to cause the medical device to reach the target based upon the computational model.

31. The method according to claim 30 wherein determining the inputs necessary to the navigation system to cause the elongate medical device to reach the target based upon a computational physics-based model of the elongate medical device and the navigation system includes determining the magnetic field strength needed to cause the medical device to reach the target based upon the computational physics-based model.

32. The method according to claim 30 wherein the user makes inputs remotely from the subject.

33. The method according to claim 30 wherein the step of displaying a virtual representation of the distal end portion of the elongate medical device includes superposing the representation of the end portion of the elongate medical device over a representation of the operating region in the subject.

34. The method according to claim 33 wherein the representation of the operating region in the subject is derived from an x-ray image.

35. The method according to claim 33 wherein the representation of the operating region in the subject is derived from a CT image.

36. The method according to claim 33 wherein the representation of the operating region in the subject is derived from an MR image.

37. The method according to claim 33 wherein the representation of the operating region in the subject is derived from an ultrasound image.

38. The method according to claim 33 wherein the representation of the operating region in the subject is derived from a map of points on surfaces in the operating region.

39. The method according to claim 27 wherein the navigation system comprises at least one external magnet for applying a magnetic field to a magnetically responsive element on the elongate medical device, and wherein the control inputs include changes in the magnetic field direction.

40. The method according to claim 27 wherein the navigation system comprises elements in the medical device which, when operated by the navigation system, change the configuration of the distal end portion of the medical device.

41. The method according to claim 40 wherein at least some of the elements which change the configuration of the distal end portion of the medical device are electrostrictive elements.

42. The method according to claim 40 wherein at least some of the elements which change the configuration of the distal end portion of the medical device are magnetostrictive elements.

43. The method according to claim 40 wherein the navigation system comprises mechanical links in the medical device which, when translated, change the configuration of the distal end portion of the medical device.

44. The method according to claim 27 wherein the step of operating the navigation system occurs automatically after the inputs by the user are accepted.

45. The method according to claim 27 wherein the step of operating the navigation system only occurs after an input by the user.

46. The method according to claim 27 wherein the computational physics-based model is based at least in part on the physical characteristics of the medical device.

47. The method according to claim 46 wherein the computational physics-based model is based at least in part on a mathematical representation of at least one physical characteristic of the medical device.

48. The method according to claim 46 wherein the computational physics-based model is based at least in part on measurements of at least one physical characteristic of the medical device.

49. A method of navigating the distal end of a medical device having a magnetically responsive element through the application of a magnetic field from an external source magnet, the method comprising:
identifying a plurality of points on an image of the distal end portion of the medical device while a known magnetic field is applied to the distal end portion of the medical device;
processing the identified points to determine at least one geometrical characteristic of the distal end of the medical device;
allowing the user to input a desired magnetic field;

displaying a virtual representation of the distal end of the medical device as if the desired magnetic field were applied based upon a calculation incorporating the at least one geometrical characteristic; and allowing the user to input an instruction to apply the desired magnetic field and reorient the medical device.

50. A method of navigating the distal end of a flexible medical device having actuation elements controlled by applying a set of actuation controls, the method comprising:

displaying a virtual representation of the distal end portion of the medical device;

in response to inputs of desired changes in the shape and orientation of the distal end of the medical device that can be effected by changing the applied actuation controls, updating the displayed virtual representation of the distal end portion of the medical device by using a computational physics-based model for device deformation together with device properties; and in response to an input by the user, applying a set of actuation controls which is based upon the properties of the distal end portion of the medical device that will configure the distal end in the desired shape and orientation.

51. A method of specifying a set of actuation controls to apply to a set of remotely actuated elements at the distal end of a flexible medical device in an operating region in a patient, the method comprising:

identifying points on the distal end of the medical device on an image of the operating region;

based upon information about the distal end of the medical device from the identified points, displaying a reconstructed virtual image of the medical device that can be computationally manipulated as if a new magnetic field were applied to the device;

accepting inputs from the user to change the configuration of the virtual image of the medical device; and applying actuation controls to actuate the actual medical device in the operating region as computed from a combination of user-specified inputs and a computational physics-based model of device physics, corresponding to the user-manipulated virtual image.

52. A method of specifying a set of actuation controls to apply to a set of remotely actuated elements at the distal end of a flexible medical device in an operating region in a patient, the method comprising:

identifying points on the distal end of the medical device on an image of the operating region;

based upon information about the distal end of the medical device from the identified points, displaying a reconstructed virtual image of the medical device that can be computationally manipulated as if a new magnetic field were applied to the device;

accepting inputs from the user identifying a target location on the image of the operating region that the user desires the device tip to reach; and applying actuation controls to actuate the actual medical device in the operating region as computed from a combination of user-specified inputs and a computational model of device physics, corresponding to the user-specified target location.

53. A method of specifying a set of actuation controls to apply to a set of remotely actuated elements at the distal end of a flexible medical device in an operating region in a patient, the method comprising:

reconstructing the current device configuration from device localization data at one or more points on the device;

displaying a reconstructed virtual image of the medical device that can be computationally manipulated as if a new set of actuation controls were applied to the device;

accepting inputs from the user to change the configuration of the virtual image of the medical device; and applying actuation controls to actuate the actual medical device in the operating region as computed from a combination of user-specified inputs and a computational model of device physics, corresponding to the user-manipulated virtual image.

54. A method of specifying a set of actuation controls to apply to a set of remotely actuated elements at the distal end of a flexible medical device, the method comprising:

reconstructing the current device configuration from device localization data at one or more points on the device;

displaying a reconstructed virtual image of the medical device that can be computationally manipulated as if a new set of actuation controls were applied to the device;

accepting inputs from the user to identify a target location on the display that the user desires the device tip to reach; and applying actuation controls to actuate the actual medical device in the operating region as computed form a combination of user-specified inputs and a computational model of device physics, corresponding to the user-specified target location.

55. A method of navigating the distal end of a flexible medical device having a set of remotely actuated elements through the application of a remote set of actuation controls, the method comprising:

identifying a plurality of points on two projected images of the distal end portion of the medical device while a known (or zero) set of actuation controls is applied to the distal end portion of the medical device;

identifying a desired location for the tip of the device on one or both planes of projected images of the device and its operating environment, or on a three-dimensional regional electrical map or its projections;

calculating with a computer, based upon the elastic and magnetic properties of the device and automatically drawing one or more of: (a) a locus of possible locations of the medial device tip within the plane of the distal device tip, shown on one or both planes of the projected images(s); (b) an accessible surface of possible locations that can be accessed by the device tip by a combination of deflection and axial rotation, shown on one or both planes of the projected image(s); or (c) said locus or accessible surface rendered together with device tip in a three-dimensional graphical view;

identifying a desired location for the tip of the device as a point on said locus or on said accessible surface in either image plane, three dimensional graphical view, or regional electrical activity map;

computing a set of actuation controls and device advancement/retraction that will enable the device to assume a configuration to closely reach the desired tip location;

controlling advancement and retraction of said device with a computer-controlled device advancer;

instructing the computer to automatically advance the device to the selected point by application of appropriate actuation controls and device advancer movements; and displaying one or more of (a) a new set of projected images of the device and its operating environment, or (b) a new three-dimensional regional electrical map or its projections.

56. A method of navigating the distal end of a flexible medical device having a set of remotely actuated elements through the application of a set of actuation controls, the method comprising:

identifying a plurality of points on two projected images of the distal end portion of the medical device while a known (or zero) set of actuation controls is applied to the distal end portion of the medical device;

identifying a desired location for the tip of the device on one or both planes of projected images of the device and its operating environment, or on a three-dimensional region electrical map or its projections;

calculating with a computer, based upon the elastic and magnetic properties of the device and automatically drawing one or more of: (a) a locus of possible locations of the medical device tip within the plan of the distal device tip, shown on one or both planes of the bi-plane image; (b) an accessible surface of possible locations that can be accessed by the device tip by a combination of deflection and axial rotation, shown on one or both planes of the projected image(s); or (c) said locus or accessible surface rendered together with device tip in a three-dimensional graphical view;

identifying a desired location for the tip of the device as a point that is beyond said locus or said accessible surface in either image plane, three-dimensional graphical view, or regional electrical activity map;

computing a set of actuation controls and device advancement/retraction that will enable the device to assume a configuration to closely reach the desired tip location;

controlling advancement and retraction of said device with a computer-controlled device advancer;

instructing the computer to automatically advance the device to the selected point by application of appropriate magnetic fields and device advancer movements; and displaying one or more of (a) a new set of projected images of the device and its operating environment, or (b) a new three-dimensional regional electrical map or its projections.

57. A method of navigating the distal end of a magnetically guidable catheter, whose distal tip is orientable with an applied magnetic field, and whose free length from the distal end of a guide sheath is telescopingly adjustable, to a selected target point in an operating region in a subject, the method comprising:

using a computational physics-based model of the catheter and information about the position and orientation of the distal end of the guide sheath to determine the magnetic field to apply and to determine the free length to extend the catheter from the guide sheath to cause the distal end portion of the device to assume a configuration such that the distal tip reaches the target; and applying the determined magnetic field and extend the catheter from the guide sheath to the free length.

58. The method according to claim 57 further comprising displaying a virtual image of the catheter as if the determined magnetic field was applied to the distal tip and the catheter was extended to the determined free length.

59. The method according to claim 58 further comprising applying the determined magnetic field to the distal tip and extending the catheter from the guide sheath to the determined free length. reach the target point.

60. A method of navigating the distal end of an orientable catheter, whose distal tip is orientable with an applied control variable, and whose free length from the distal end of a guide sheath is telescopingly adjustable, to a selected target point in an operating region in a subject, the method comprising:

using a computational physics-based model of the catheter and information about the position and orientation of the distal end of the guide sheath to determine the control variable to apply and to determine the free length to extend the catheter from the guide sheath to cause the distal end portion of the device to assume a configuration such that the distal tip reaches the target point; and applying the determined magnetic field and extend the catheter from the guide sheath to the free length.

* * * * *

UNITED STATES PATENT AND TRADEMARK OFFICE
CERTIFICATE OF CORRECTION

PATENT NO.        : 7,630,752 B2                                        Page 1 of 1
APPLICATION NO.   : 10/448273
DATED             : December 8, 2009
INVENTOR(S)       : Raju R. Viswanathan It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1927 days.

Signed and Sealed this

Second Day of November, 2010

David J. Kappos
*Director of the United States Patent and Trademark Office*